United States Patent [19]
Griffith et al.

(10) Patent No.: US 11,426,492 B2
(45) Date of Patent: Aug. 30, 2022

(54) COLLAGEN AND COLLAGEN LIKE PEPTIDE BASED HYRDOGELS, CORNEAL IMPLANTS, FILLER GLUE AND USES THEREOF

(71) Applicant: EOSVision (Suzhou) Biomedical Technology Co., Ltd, Jiangsu Prov. (CN)

(72) Inventors: May Griffith, Montreal (CA); Ayan Samanta, Uppsala (SE); Jaganmohan Reddy Jangamreddy, Hyderabad (IN)

(73) Assignee: EOSVision (Suzhou) Biomedical Technology Co., Ltd, Jiangsu Prov. (CN)

( * ) Notice: Subject to any disclaimer, the term of this patent is extended or adjusted under 35 U.S.C. 154(b) by 417 days.

(21) Appl. No.: 16/341,726

(22) PCT Filed: Oct. 13, 2017

(86) PCT No.: PCT/IB2017/056342
§ 371 (c)(1),
(2) Date: Apr. 12, 2019

(87) PCT Pub. No.: WO2018/069873
PCT Pub. Date: Apr. 19, 2018

(65) Prior Publication Data
US 2020/0046884 A1 Feb. 13, 2020

Related U.S. Application Data

(60) Provisional application No. 62/407,650, filed on Oct. 13, 2016.

(51) Int. Cl.
| | |
|---|---|
| *A61L 27/52* | (2006.01) |
| *A61K 31/7088* | (2006.01) |
| *A61K 47/60* | (2017.01) |
| *A61K 9/00* | (2006.01) |
| *A61L 27/22* | (2006.01) |
| *C07K 14/78* | (2006.01) |
| *A61L 27/24* | (2006.01) |
| *A61L 27/26* | (2006.01) |
| *A61L 27/38* | (2006.01) |
| *A61K 38/00* | (2006.01) |

(52) U.S. Cl.
CPC ............ *A61L 27/52* (2013.01); *A61K 9/0051* (2013.01); *A61K 31/7088* (2013.01); *A61K 47/60* (2017.08); *A61L 27/225* (2013.01); *A61L 27/24* (2013.01); *A61L 27/26* (2013.01); *A61L 27/3834* (2013.01); *C07K 14/78* (2013.01); *A61K 38/00* (2013.01); *A61L 2430/16* (2013.01)

(58) Field of Classification Search
CPC ...... A61L 27/24; A61L 27/52; A61L 2430/16; A61L 27/225; A61K 38/00; A61K 47/60; A61K 9/0051; C07K 14/78; C08J 3/075; C08J 2389/00; C08J 3/24; C08L 89/06
See application file for complete search history.

(56) References Cited

U.S. PATENT DOCUMENTS

2008/0317818 A1  12/2008  Griffith

FOREIGN PATENT DOCUMENTS

WO   WO 2016/165788   * 10/2016   ............ C07K 14/78

OTHER PUBLICATIONS

Abdulhadl (Construction of Recombinant Human Collagen III Variants and Genomic Manipulations in Yeast for Collagen Yield Optimization; UC Irvine. ProQues Dissertations Publishing, 2016. 10027812 https://www.proquest.com/openvie/06b9a746cd3c22b822 faa27ea8fa1a68/1?pq-origsite=gscholar&cbl=18750. (Year: 2016).*
Islam (RSC Advance, 2016 6 55745-55749) (Year: 2016).*
D'Este (Carbohydrate Polymers 108 (2014) 239-246) (Year: 2014).*
Perez et al. (Macromol. Biosci. 2011, 11, 1426-1431) (Year: 2011).*
Extended European Search Report dated Apr. 28, 2020 in EP counterpart app, EP17860336, regional stage entry from PCT/IB2017/056342, reporting on 15 claims, all amended upon EPO regional stage entry and completely different from the original 20 claims in the parent PCT app and the US national stage entry app.

* cited by examiner

*Primary Examiner* — Anna R Falkowitz
(74) *Attorney, Agent, or Firm* — Darby IP & Law Corporation; George E. Darby

(57) ABSTRACT

The present invention provides for collagen and collagen like peptide based hydrogels, corneal implants, filler glue and uses thereof. The invention represents an advancement in the field of hydrogels, corneal implants, filler glue based on collagen and collagen like peptides. The invention discloses collagen and novel collagen like peptides crosslinked with DMTMM and their use in preparation of hydrogel, corneal implant and filler glue which are highly efficacious and robust as compared to existing corneal implants. Further, the invention relates to method of treating corneal defects and diseases.

16 Claims, 21 Drawing Sheets
Specification includes a Sequence Listing.

3 CLP-PEG          3 RHCIII-MPC

Collagen implant crosslinked with 1.0 eqv. DMTMM    Collagen implant crosslinked with 1.5 eqv. DMTMM

CLP-PEG-MPC

CLP-PEG

SEQUENCE LISTING

```
<160> NUMBER OF SEQ ID NOS: 15

<210> SEQ ID NO 1
<211> LENGTH: 13751
<212> TYPE: DNA
<213> ORGANISM: Artificial Sequence
<220> FEATURE:
<223> OTHER INFORMATION: pPINKa-HC vector (pPink-aMF-COL mimic-His-P4H-
      HC) containing the 10 repeats of collagen like peptide

<400> SEQUENCE: 1
agatctaaca tccaaagacg aaaggttgaa tgaaaccttt ttgccatccg acatccacag        60
gtccattctc acacataagt gccaaacgca acaggagggg atacactagc agcagaccgt       120
tgcaaacgca ggacctccac tcctcttctc ctcaacaccc acttttgcca tcgaaaaacc       180
agcccagtta ttgggcttga ttggagctcg ctcattccaa ttccttctat taggctacta       240
acaccatgac tttattagcc tgtctatcct ggcccccctg gcgaggttca tgtttgttta       300
tttccgaatg caacaagctc cgcattacac ccgaacatca ctccagatga gggctttctg       360
agtgtggggt caaatagttt catgttcccc aaatggccca aaactgacag tttaaacgct       420
gtcttggaac ctaatatgac aaaagcgtga tctcatccaa gatgaactaa gtttggttcg       480
ttgaaatgct aacggccagt tggtcaaaaa gaaacttcca aaagtcggca taccgtttgt       540
cttgtttggt attgattgac gaatgctcaa aaataatctc attaatgctt agcgcagtct       600
ctctatcgct tctgaacccc ggtgcacctg tgccgaaacg caaatgggga aacacccgct       660
ttttggatga ttatgcattg tctccacatt gtatgcttcc aagattctgg tgggaatact       720
gctgatagcc taacgttcat gatcaaaatt taactgttct aacccctact tgacagcaat       780
atataaacag aaggaagctg ccctgtctta aacctttttt tttatcatca ttattagctt       840
actttcataa ttgcgactgg ttccaattga caagcttttg attttaacga cttttaacga       900
caacttgaga agatcaaaaa acaactaatt attcgaaacg gaattcgaaa cgatgagatt       960
tcctagtatt ttcaccgccg tattgttcgc cgcaagttca gcattggcct gtggtcctaa      1020
gggtcctaaa ggtcctaaag gtcctaaagg tcctccaggt ccacctggtc ctcctggtcc      1080
tccaggtgac cctggtgacc ctggtgaccc aggtgaccct ggtgacagag gtgacgcagg      1140
tcctaagggt cctaaaggtc caaagggtcc taagggtcct ccaggtccac ctggtcctcc      1200
aggtcctcct ggtgaccctg gtgacccagg tgacctggt gacctggtc caaaaggtcc       1260 taagggtcca aaaggtccta aggtcctcc aggtccacca ggtcctcctg gtccaccagg      1320
```

```
tgacccaggt gaccctggtg accctggtga ccctggtggt gcagatggtg aagctggtca      1380
accaaagggt ccaaaaggtc ctaagggtcc taagggtcct cctggtcctc ctggtccacc      1440
tggtccacct ggtgacccag gtgaccctgg tgaccctggt gacccaggtg gtgcaagagg      1500
tgacgtaggt cctaaaggtc caaagggtcc taagggtcct aaaggtcctc caggtccacc      1560
tggtccacca ggtcctcctg gtgacccagg tgaccctggt gacccaggtg acccaggtgc      1620
tgcaggtgca aaaggtgaca gaggtgaaac cggtcctgct cctaagggtc aaaaggtcc       1680 taaaggtcca aagggtccac ctggtccacc tggtccacca ggtccacctg gtgaccctgg      1740
tgacccaggt gaccctggtg acccaggtgg tccaagaggt gacgctggtc ctaaaggtcc      1800
aaagggtcca aagggtccta aggtcctcc aggtcctcca ggtcctcctg gtcctccagg       1860
tgaccctggt gacccaggtg acccaggtga cccaggtcca aaaggtccaa aaggtccaaa      1920
aggtcctaag ggtccaccag gtccaccagg tccacctggt cctccaggtg acccaggtga      1980
cccaggtgac ccaggtgacc caggtccagc tggtaaatct ggtgacagag gtgaaacagg      2040
tccagctcca aaaggtccta aggtgccaaa gggtccaaag gtccaccag gtcctccagg       2100 tccaccaggt cctcctggtg acccaggtga cccaggtgac cctggtgacc ctggtggtgc      2160
tagaggtgac gcaggtccaa aggtcctaa gggtccaaa ggtccaaaag gtccacctgg        2220
tccaccaggt cctccaggtc caccaggtga cccaggtgac caggtgacc caggtgaccc      2280 aggtcatcat catcatcatc attgaggtac cggccggcca tttaaataca ggccccttt      2340 cctttgtcga tatcatgtaa ttagttatgt cacgcttaca ttcacgccct cctcccacat     2400
ccgctctaac cgaaaaggaa ggagttagac aacctgaagt ctaggtccct atttatttt     2460 tttaatagtt atgttagtat taagaacgtt atttatattt caaattttc tttttttct      2520 gtacaaacgc gtgtacgcat gtaacattat actgaaaaacc ttgcttgaga aggttttggg   2580
acgctcgaag gctttaattt gcaagctgga tccatgagtc acaatctgct tccacagacg    2640
agtacaagga caggcaaaag gaattggaag aagttgctaa cccaataatg agcaagttct    2700
atggagctgc tggtggagct cctggtggag ctcctggtgg cttccctgga ggtttccctg    2760
gcggagctgc gcagctggc ggtgccccag gtggtgctgc cccaggcgga gacagcggac     2820
caaccgtgga agaagtcgat taagcaattc aacggataaa ttctggttaa tatatataac    2880
gtgaatagga aattaaggaa attttggatc taataatgtg ctgtatgccg acatcgggca    2940
tcgtagattg tatagtatcg ctgacactat aataagccag ccaaaacccc taaaccagtt    3000
gccctccact aattagtgta ctacccaatc ttgcctcttc gggtgtcttt tataaggaca    3060
gattcacaag ctcttgttgc ccaatacaca catacacaca gagataatag cagtcccgcg    3120
ggaaacgatg agatttccta gtatttttac agcagttctt tttgcagcct cctccgcatt    3180
ggcacatcct ggtttcttca cctccatcgg tcagatgaca gatttgattc ataccgaaaa    3240
ggaccttgtt acttctttga aggattacat caaggctgaa gaggacaagt tggaacaaat    3300
caagaaatgg gcagagaaac ttgatagatt gacctccact gctacaaagg acccagaagg    3360
ttttgttgga cacccctgtca acgctttcaa acttatgaag agattgaaca cagagtggag    3420
tgaattggag aatcttgttt tgaaggatat gtcagacgtt tttattagta accttaccat    3480
ccaaagacca gtcttgtcaa atgatgaaga ccaggttgga gctgccaaag ctttgcttag    3540
acttcaagat acttacaact tggataccga cactattagt aagggtaatt tgcctggagt    3600
caaacataag tcttttctta cagcagaaga ttgtttcgag ttgggtaaag ttgcatacac    3660
tgaagctgac tactatcaca cagaattgtg gatggagcaa gcccttagac agttggatga    3720
```

```
aggagagatt tctaccatcg ataaagtttc cgtccttgac tacttgtcat atgccgttta   3780
ccaacaggga gatttggaca aggcattgct tttgactaag aaacttttgg aacttgatcc   3840
agagcatcaa agagctaacg gtaatttgaa gtacttcgaa tacattatgg ctaaagagaa   3900
ggatgttaac aaatctgcct ccgatgacca atccgaccag aagactacac caagaaaaaa   3960
gggagttgct gtcgattatc ttcctgaaag acaaaaatac gagatgttgt gtagaggtga   4020
aggaattaag atgacaccaa gaagacagaa aaagttgttt tgcagatatc atgatggtaa   4080
cagaaaccca aaattcatct tggcccctgc aaagcaagaa gatgagtggg acaaacctag   4140
aattatcaga ttccacgata ttatctccga cgctgaaatt gagatcgtca agatcttgc    4200 taagccaaga ttgagaagag ccactatttc aaatcctatc actggtgact tggaaacagt   4260
tcattacaga atctcaaaga gtgcttggtt gtccggatac gagaacccag ttgtctcaag   4320
aattaatatg agaatccagg atcttactgg tttggacgtt tctactgccg aagagttgca   4380
agtcgcaaac tatggagttg gtggacagta cgaaccacac tttgatttcg caagaaagga   4440
tgaacctgac gctttcaaag agcttggtac aggaaataga attgctacct ggttgtttta   4500
catgtctgac gtctccgctg gtggagccac cgtttttccca gaagtcggtg cctcagtttg   4560
gcctaaaaag ggtactgctg ttttctggta taatttgttc gcaagtggag agggagatta   4620
ctctactaga cacgcagctt gccctgtttt ggtcggtaac aaatgggttt ctaataagtg   4680
gcttcacgag agaggacagg agttcagaag accttgcaca ctttccgagt tggagtaggt   4740
cgaccttgct agattctaat caagaggatg tcagaatgcc atttgcctga gagatgcagg   4800
cttcattttt gatacttttt tatttgtaac ctatatagta taggattttt tttgtcattt   4860
tgtttcttct cgtacgagct tgctcctgat cagcctatct cgcagctgat gaatatcttg   4920
tggtaggggt ttgggaaaat cattcgagtt tgatgttttt cttggtattt cccactcctc   4980
ttcagagtac agaagattaa gtgagaagtt cgtttgtgca agcttaatga gtcacaatct   5040
gcttccacag acgagtacaa ggacaggcaa aaggaattgg aagaagttgc taacccaata   5100
atgagcaagt tctatggagc tgctggtgga gctcctggtg gagctcctgg tggcttccct   5160
ggaggtttcc ctggcggagc tggcgcagct ggcggtgccc caggtggtgc tgccccaggc   5220
ggagacagcg gaccaaccgt ggaagaagtc gattaagcaa ttcaacggat aaattctggt   5280
taatatatat aacgtgaata ggaaattaag gaaattttgg atctaataat gtgctgtatg   5340
ccgacatcgg gcatcgtaga ttgtatagta tcgctgacac tataataagc cagccaaaac   5400 ccctaaaacca gttgccctcc actaattagt gtactaccca atcttgcctc ttcgggtgtc   5460
ttttataagg acagattcac aagctcttgt tgcccaatac acacatacac acagagataa   5520
tagcagtcct cgaggaaacg atgagattcc catccatttt taccgcagtc ttgttcgccg   5580
catccagtgc tttggctgac gcccctgagg aggaggacca tgtcttggtc ttgagaaagt   5640
ctaactttgc cgaggcactt gctgccata agtactgct tgttgaattt tacgctccat   5700
ggtgtggtca ctgcaaggct ttggcccctg aatacgccaa agctgctggt aaattgaaag   5760
cagagggatc tgaaattaga cttgccaagg tcgatgcaac cgaagagtcc gacttggccc   5820
aacagtacgg tgttagagga tatccaacta ttaagttttt cagaaacgga gataccgcat   5880
ctcctaaaga gtatactgct ggaagagaag ccgatgacat cgttaattgg ttgaagaaaa   5940
gaactggtcc agccgcaact acattgcctg atggagctgc cgcagaatcc cttgtcgagt   6000
cttccgaagt tgctgtcatt ggtttctttta aggatgttga gtcagacagt gctaaacaat   6060
```

```
ttttgcaggc tgccgaagcc attgatgaca tcccatttgg tatcacttct aattccgatg    6120
ttttctcaaa gtaccaattg gataaagacg gagttgtcct ttttaagaaa ttcgatgagg    6180
gtagaaacaa ttttgaggga gaagtcacaa aggaaaactt gcttgacttc atcaagcata    6240
accaattgcc acttgttatc gagtttaccg aacagactgc tcctaagatt ttcggtggag    6300
aaattaaaac tcacatcttg ttgttttttgc ctaagtcagt tagtgattac gacggtaaat    6360
tgtctaactt caagacagca gctgagtcct tcaagggaaa aatcttgttt attttcatcg    6420
attccgacca taccgataac caaagaatct tggaattttt cggtcttaag aaagaagagt    6480
gtccagccgt tagattgatt actcttgaag aggaaatgac aaagtataaa cctgagtcag    6540
aggaattgac agctgagaga attaccgaat tttgccatag attcttggaa ggtaaaatta    6600
agccacactt tgatgagtca agagcttccag aagattggga caagcagcct gttaaagtct    6660
tggttggtaa aaactttgag gatgttgctt tcgacgaaaa gaaaaatgtc ttcgttgaat    6720
tttacgcacc atggtgtggt cattgcaagc aattggctcc tatttgggat aagcttggag    6780
agacttataa agaccacgaa acattgtcea tegctaaaat ggattcaact gcaaatgagg    6840
ttgaagctgt caaggttcac tcatttccaa cattgaaatt ttteectgea agtgetgata    6900 gaacagttat tgactataac ggagagagaa ccttggatgg ttttaagaag ttccttgaaa    6960
gtggtggaca ggatggtgct ggagatgacg atgacttgga agaccttgag gaagccgaag    7020
agcctgatat ggaagaagac gatgaccaaa aagccgttca cgacgagttg tagaccggtc    7080
ttgctagatt ctaatcaaga ggatgtcaga atgccatttg cctgagagat gcaggcttca    7140
tttttgatac tttttttattt gtaacctata tagtatagga ttttttttgt cattttgttt    7200
cttctcgtac gagcttgctc ctgatcagcc tatctcgcag ctgatgaata tcttgtggta    7260
ggggtttggg aaaatcattc gagtttgatg ttttctcttgg tatttcccac tcctcttcag    7320
agtacagaag attaagtgag aagttcgttt gtgcaagctt agcggccgcc ttccaaactc    7380
tcatggattc tcaggtaata ggtattctag gaggaggcca gctaggccga atgattgttg    7440
aggccgctag caggctcaat atcaagaccg tgattcttga tgatggtttt tcacctgcta    7500
agcacattaa tgctgcgcaa gaccacatcg acggatcatt caaagatgag gaggctatcg    7560
ccaagttagc tgccaaatgt gatgttctca ctgtagagat tgagcatgtc aacacagatg    7620
ctctaaagag agttcaagac agaactggaa tcaagatata tcetttacca gagacaatcg    7680 aactaatcaa ggataagtac ttgcaaaagg aacatttgat caagcacaac atttcggtga    7740
caaagtctca gggtatagaa tctaatgaaa aggcgctgct tttgtttgga gaagagaatg    7800
gatttccata tctgttgaag tcccggacta tggcttatga tggaagaggc aattttgtag    7860
tggagtctaa agaggacatc agtaaggcat tagagttctt gaaagatcgt ccattgtatg    7920
ccgagaagtt tgctcctttt gttaaagaat tagcggtaat ggttgtgaga tcactggaag    7980
gcgaagtatt ctcctaccca accgtagaaa ctgtgcacaa ggacaatatc tgtcatattg    8040
tgtatgctcc ggccagagtt aatgacacca tccaaaagaa agctcaaata ttagctgaaa    8100
acactgtgaa gactttccca ggcgctggaa tcttcggagt tgagatgttc ctattgtctg    8160
atggagaact tcttgtaaat gagattgctc caaggcccca caattctggt cactatacaa    8220
tcgatgcatg tgtaacatct cagttcgaag cacatgtaag agccataact ggtctgccaa    8280
tgccactaga tttcaccaaa ctatctactt ccaacaccaa cgctattatg ctcaatgttt    8340
tgggtgctga aaaatctcac ggggaattag agttttgtag aagagcctta gaaacacccg    8400
gtgcttctgt atatctgtac ggaaagacca cccgattggc tcgtaagatg ggtcatatca    8460
```

```
acataatagg atcttccatg ttggaagcag aacaaaagtt agagtacatt ctagaagaat    8520
caacccactt accatccagt actgtatcag ctgacactaa accgttggtt ggagttatca    8580
tgggttcaga ctctgatcta cctgtgattt cgaaaggttg cgatatttta aaacagtttg    8640
gtgttccatt cgaagttact attgtctctg ctcatagaac accacagaga atgaccagat    8700
atgcctttga agccgctagt agaggtatca aggctatcat tgcaggtgct ggtggtgctg    8760
ctcatcttcc aggaatggtt gctgccatga ctccgttgcc agtcattggt gttcctgtca    8820
agggctctac gttggatggt gtagactcgc tacactcgat tgtccaaatg cctagaggtg    8880
ttcctgtggc tacggttgct atcaacaacg ccaccaatgc cgctctgttg gccatcagga    8940
ttttaggtac aattgaccac aaatggcaaa aggaaatgtc caagtatatg aatgcaatgg    9000
agaccgaagt gttggggaag gcatccaact tggaatctga agggtatgaa tcctatttga    9060
agaatcgtct ttgaatttag tattgttttt taatagatgt atatataata gtacacgtaa    9120
cttatctatt ccattcataa tttttatttta aaggttcggt agaaatttgt cctccaaaaa    9180
gttggttaga gcctggcagt tttgataggc attattatag attgggtaat atttaccctg    9240
cacctggagg aactttgcaa agagcctcat gtgcggcgcg ccaggccata atggccaaac    9300
ggtttctcaa ttactatata ctactaacca tttacctgta gcgtatttct tttccctctt    9360
cgcgaaagct caagggcatc ttcttgactc atgaaaaata tctggatttc ttctgacaga    9420
tcatcaccct tgagcccaac tctctagcct atgagtgtaa gtgatagtca tcttgcaaca    9480
gattattttg gaacgcaact aacaaagcag atacaccctt cagcagaatc ctttctggat    9540
attgtgaaga atgatcgcca aagtcacagt cctgagacag ttcctaatct ttaccccatt    9600
tacaagttca tccaatcaga cttcttaacg cctcatctgg cttatatcaa gcttaccaac    9660
agttcagaaa ctcccagtcc aagtttcttg cttgaaagtg cgaagaatgg tgacaccgtt    9720
gacaggtaca cctttatggg acattccccc agaaaaataa tcaagactgg gcctttagag    9780
ggtgctgaag ttgaccccctt ggtgcttctg gaaaaagaac tgaagggcac cagacaagcg    9840
caacttcctg gtattcctcg tctaagtggt ggtgccatag gatacatctc gtacgattgt    9900
attaagtact ttgaaccaaa aactgaaaga aaactgaaag atgttttgca acttccggaa    9960
gcagctttga tgttgttcga cacgatcgtg gcttttgaca atgtttatca aagattccag   10020
gtaattggaa acgtttctct atccgttgat gactcggacg aagctattct tgagaaatat   10080
tataagacaa gagaagaagt ggaaaagatc agtaaagtgg tatttgacaa taaaactgtt   10140
ccctactatg aacagaaaga tattattcaa ggccaaacgt tcacctctaa tattggtcag   10200
gaagggtatg aaaaccatgt tcgcaagctg aaagaacata ttctgaaagg agacatcttc   10260
caagctgttc cctctcaaag ggtagccagg ccgacctcat tgcacccttt caacatctat   10320
cgtcatttga gaactgtcaa tccttctcca tacatgttct atattgacta tctagacttc   10380
caagttgttg gtgcttcacc tgaattacta gttaaatccg acaacaacaa caaaatcatc   10440
acacatccta ttgctggaac tcttcccaga ggtaaaacta tcgaagagga cgacaattat   10500
gctaagcaat tgaagtcgtc tttgaaagac agggccgagc acgtcatgct ggtagatttg   10560
gccagaaatg atattaaccg tgtgtgtgag cccaccagta ccacggttga tcgtttattg   10620
actgtggaga gattttctca tgtgatgcat cttgtgtcag aagtcagtgg aacattgaga   10680
ccaaacaaga ctcgcttcga tgctttcaga tccattttcc cagcaggaac cgtctccggt   10740
gctccgaagg taagagcaat gcaactcata ggagaattgg aaggagaaaa gagaggtgtt   10800
```

```
tatgcgggggg ccgtaggaca ctggtcgtac gatggaaaat cgatggacac atgtattgcc    10860
ttaagaacaa tggtcgtcaa ggacggtgtc gcttaccttc aagccggagg tggaattgtc    10920
tacgattctg accccctatga cgagtacatc gaaaccatga acaaaatgag atccaacaat    10980
aacaccatct tggaggctga gaaaatctgg accgataggt tggccagaga cgagaatcaa    11040
agtgaatccg aagaaaacga tcaatgaacg gaggacgtaa gtaggaattt atggtttggc    11100
cataatggcc tagcttggcg taatcatggt catagctgtt tcctgtgtga aattgttatc    11160
cgctcacaat tccacacaac atacgagccg gaagcataaa gtgtaaagcc tggggtgcct    11220
aatgagtgag ctaactcaca ttaattgcgt tgcgctcact gcccgctttc cagtcgggaa    11280
acctgtcgtg ccagctgcat taatgaatcg gccaacgcgc ggggagaggc ggtttgcgta    11340
ttgggcgctc ttccgcttcc tcgctcactg actcgctgcg ctcggtcgtt cggctgcggc    11400
gagcggtatc agctcactca aaggcggtaa tacggttatc cacagaatca ggggataacg    11460
caggaaagaa catgtgagca aaaggccagc aaaaggccag gaaccgtaaa aaggccgcgt    11520
tgctggcgtt tttccatagg ctccgccccc ctgacgagca tcacaaaaat cgacgctcaa    11580
gtcagaggtg gcgaaacccg acaggactat aaagatacca ggcgtttccc cctggaagct    11640
ccctcgtgcg ctctcctgtt ccgacccctgc cgcttaccgg atacctgtcc gcctttctcc    11700
cttcgggaag cgtggcgctt tctcatagct cacgctgtag gtatctcagt tcggtgtagg    11760
tcgttcgctc caagctgggc tgtgtgcacg aaccccccgt tcagcccgac cgctgcgcct    11820
tatccggtaa ctatcgtctt gagtccaacc cggtaagaca cgacttatcg ccactggcag    11880
cagccactgg taacaggatt agcagagcga ggtatgtagg cggtgctaca gagttcttga    11940
agtggtggcc taactacggc tacactagaa ggacagtatt tggtatctgc gctctgctga    12000
agccagttac cttcggaaaa agagttggta gctcttgatc cggcaaacaa accaccgctg    12060
gtagcggtgg tttttttgtt tgcaagcagc agattacgcg cagaaaaaaa ggatctcaag    12120
aagatccttt gatcttttct acggggtctg acgctcagtg gaacgaaaac tcacgttaag    12180
ggattttggt catgagatta tcaaaaagga tcttcaccta gatccttttaa aattaaaaat    12240 gaagttttaa atcaatctaa agtatatatg agtaaacttg gtctgacagt taccaatgct    12300
taatcagtga ggcacctatc tcagcgatct gtctatttcg ttcatccata gttgcctgac    12360
tccccgtcgt gtagataact acgatacggg agggcttacc atctggcccc agtgctgcaa    12420
tgataccgcg agacccacgc tcaccggctc cagatttatc agcaataaac cagccagccg    12480
gaagggccga gcgcagaagt ggtcctgcaa ctttatccgc ctccatccag tctattaatt    12540
gttgccggga agctagagta agtagttcgc cagttaatag tttgcgcaac gttgttgcca    12600
ttgctacagg catcgtggtg tcacgctcgt cgtttggtat ggcttcattc agctccggtt    12660
cccaacgatc aaggcgagtt acatgatccc ccatgttgtg caaaaaagcg gttagctcct    12720
tcggtcctcc gatcgttgtc agaagtaagt tggccgcagt gttatcactc atggttatgg    12780
cagcactgca taattctctt actgtcatgc catccgtaag atgcttttct gtgactggtg    12840
agtactcaac caagtcattc tgagaatagt gtatgcggcg accgagttgc tcttgcccgg    12900
cgtcaatacg ggataatacc gcgccacata gcagaacttt aaaagtgctc atcattggaa    12960
aacgttcttc ggggcgaaaa ctctcaagga tcttaccgct gttgagatcc agttcgatgt    13020
aacccactcg tgcacccaac tgatcttcag catctttttac tttcaccagc gtttctgggt    13080
gagcaaaaac aggaaggcaa aatgccgcaa aaaagggaat aagggcgaca cggaaatgtt    13140
gaatactcat actcttcctt tttcaatatt attgaagcat ttatcagggt tattgtctca    13200
```

```
tgagcggata catatttgaa tgtatttaga aaaataaaca aatagggggtt ccgcgcacat   13260 ttccccgaaa agtgccacct gacgtctaag aaaccattat tatcatgaca ttaacctata   13320
aaaataggcg tatcacgagg cccttcgtc tcgcgcgttt cggtgatgac ggtgaaaacc   13380
tctgacacat gcagctcccg gagacggtca cagcttgtct gtaagcggat gccgggagca   13440
gacaagcccg tcagggcgcg tcagcgggtg ttggcgggtg tcggggctgg cttaactatg   13500
cggcatcaga gcagattgta ctgagagtgc accatatgcg gtgtgaaata ccgcacagat   13560
gcgtaaggag aaaataccgc atcaggcgcc attcgccatt caggctgcgc aactgttggg   13620
aagggcgatc ggtgcgggcc tcttcgctat tacgccagct ggcgaaaggg ggatgtgctg   13680
caaggcgatt aagttgggta acgccagggt tttcccagtc acgacgttgt aaaacgacgg   13740
ccagtgaatt g                                                       13751
```

<210> SEQ ID NO 2
<211> LENGTH: 31
<212> TYPE: DNA
<213> ORGANISM: Artificial Sequence
<220> FEATURE:
<223> OTHER INFORMATION: Forward Primer

<400> SEQUENCE: 2

```
gccgcatatg agatttccta gtattttcac c                                    31
```

<210> SEQ ID NO 3
<211> LENGTH: 31
<212> TYPE: DNA
<213> ORGANISM: Artificial Sequence
<220> FEATURE:
<223> OTHER INFORMATION: Reverse Primer

<400> SEQUENCE: 3

```
gccgtctaga ggtacctcaa tgatgatgat g                                    31
```

<210> SEQ ID NO 4
<211> LENGTH: 1554
<212> TYPE: DNA
<213> ORGANISM: Artificial Sequence
<220> FEATURE:
<223> OTHER INFORMATION: Nucleic acid sequence of one repeat of collagen
      like peptide

<400> SEQUENCE: 4

```
catcctggtt tcttcacctc catcggtcag atgacagatt tgattcatac cgaaaaggac     60
cttgttactt cttgaagga ttacatcaag gctgagagg acaagttgga acaaatcaag      120
aaatgggcag agaaacttga tagattgacc tccactgcta caaggaccc agaaggtttt    180 gttggacacc ctgtcaacgc tttcaaactt atgaagagat tgaacacaga gtggagtgaa    240
ttggagaatc ttgttttgaa ggatatgtca gacggtttta ttagtaacct taccatccaa    300
agaccagtct tgtcaaatga tgaagaccag gttggagctg ccaaagcttt gcttagactt    360
caagatactt acaacttgga taccgacact attagtaagg gtaatttgcc tggagtcaaa    420
cataagtctt ttcttacagc agaagattgt ttcgagttgg gtaaagttgc atacactgaa    480
gctgactact atcacacaga attgtggatg gagcaagccc ttagacagtt ggatgaagga    540
gagatttcta ccatcgataa agtttccgtc cttgactact tgtcatatgc cgtttaccaa    600
cagggagatt tggacaaggc attgcttttg actaagaaac ttttggaact tgatccagag    660
catcaaagag ctaacggtaa tttgaagtac ttcgaataca ttatggctaa agagaaggat    720
```

```
gttaacaaat ctgcctccga tgaccaatcc gaccagaaga ctacaccaaa gaaaaaggga      780
gttgctgtcg attatcttcc tgaaagacaa aaatacgaga tgttgtgtag aggtgaagga      840
attaagatga caccaagaag acagaaaaag ttgttttgca gatatcatga tggtaacaga      900
aacccaaaat tcatcttggc ccctgcaaag caagaagatg agtgggacaa acctagaatt      960
atcagattcc acgatattat ctccgacgct gaaattgaga tcgtcaaaga tcttgctaag     1020
ccaagattga gaagagccac tatttcaaat cctatcactg gtgacttgga aacagttcat     1080
tacagaatct caaagagtgc ttggttgtcc ggatacgaga acccagttgt ctcaagaatt     1140
aatatgagaa tccaggatct tactggtttg gacgtttcta ctgccgaaga gttgcaagtc     1200
gcaaactatg gagttggtgg acagtacgaa ccacactttg atttcgcaag aaaggatgaa     1260
cctgacgctt tcaaagagct tggtacagga aatagaattg ctacctggtt gttttacatg     1320
tctgacgtct ccgctggtgg agccaccgtt ttcccagaag tcggtgcctc agtttggcct     1380
aaaaagggta ctgctgtttt ctggtataat ttgttcgcaa gtggagaggg agattactct     1440
actagacacg cagcttgccc tgttttggtc ggtaacaaat gggtttctaa taagtggctt     1500
cacgagagag acaggagtt cagaagacct tgcacacttt ccgagttgga gtag            1554
```

```
<210> SEQ ID NO 5
<211> LENGTH: 38
<212> TYPE: PRT
<213> ORGANISM: Artificial Sequence
<220> FEATURE:
<223> OTHER INFORMATION: Collagen Mimetic Peptide
<220> FEATURE:
<221> NAME/KEY: MISC_FEATURE
<222> LOCATION: (1)..(38)
<223> OTHER INFORMATION: wherein X is hydroxyproline

<400> SEQUENCE: 5

Cys Gly Pro Lys Gly Pro Lys Gly Pro Lys Gly Pro Lys Gly Pro Xaa
1               5                   10                  15

Gly Pro Xaa Gly Pro Xaa Gly Pro Xaa Gly Asp Xaa Gly Asp Xaa Gly
            20                  25                  30

Asp Xaa Gly Asp Xaa Gly
        35

<210> SEQ ID NO 6
<211> LENGTH: 16
<212> TYPE: PRT
<213> ORGANISM: Artificial Sequence
<220> FEATURE:
<223> OTHER INFORMATION: MMP Motif

<400> SEQUENCE: 6

Gly Gly Gly Gly Ser Pro Leu Gly Leu Trp Ala Gly Gly Gly Gly Ser
1               5                   10                  15

<210> SEQ ID NO 7
<211> LENGTH: 207
<212> TYPE: DNA
<213> ORGANISM: Artificial Sequence
<220> FEATURE:
<223> OTHER INFORMATION: Nucleic Acid encoding CLP with MMP Motif

<400> SEQUENCE: 7
catatgtgtg gccgaaagg tcccaagggt ccaaaagggc caagggtcc acccggaccg       60 ccgggacccc ctggaccccc cggtgatcca ggtgatcctg agaccctgg tgaccccggt      120
```

```
ggaggcggtg ggcgtccgct tgattatggg gctggggggtg gaggacgcgg gggcggaggt      180
catcaccatc atcatcacta atctaga                                          207
```

<210> SEQ ID NO 8
<211> LENGTH: 12
<212> TYPE: PRT
<213> ORGANISM: Artificial Sequence
<220> FEATURE:
<223> OTHER INFORMATION: Anti-inflammatory peptide motif

<400> SEQUENCE: 8

```
Gly Gly Gly Gly Ser Arg Tyr Thr Val Glu Leu Ala
1               5                   10
```

<210> SEQ ID NO 9
<211> LENGTH: 162
<212> TYPE: DNA
<213> ORGANISM: Artificial Sequence
<220> FEATURE:
<223> OTHER INFORMATION: Nucleic acid encoding CLP with anti-
      inflammatory motif

<400> SEQUENCE: 9

```
catatgtgtg gtcctaaggg tcctaaaggt cctaaaggtc ctaaaggtcc tccaggtcca       60
cctggtcctc ctggtcctcc aggtgaccct ggtgaccctg gtgacccagg tgaccctggt      120 ggggggggggg ggaggtatac ggtggagttg gcgtaatcta ga                        162
```

<210> SEQ ID NO 10
<211> LENGTH: 61
<212> TYPE: PRT
<213> ORGANISM: Artificial Sequence
<220> FEATURE:
<223> OTHER INFORMATION: Fusion polypeptide encoding CLP containing MMP
      and anti-inflammatory motifs
<220> FEATURE:
<221> NAME/KEY: MISC_FEATURE
<222> LOCATION: (1)..(61)
<223> OTHER INFORMATION: wherein X is hydroxyproline

<400> SEQUENCE: 10

```
Cys Gly Pro Lys Gly Pro Lys Gly Pro Lys Gly Pro Lys Gly Pro Xaa
1               5                   10                  15

Gly Pro Xaa Gly Pro Xaa Gly Pro Xaa Gly Asp Xaa Gly Asp Xaa Gly
            20                  25                  30

Asp Xaa Gly Asp Xaa Gly Gly Gly Gly Ser Pro Leu Gly Leu Trp
        35                  40                  45

Ala Gly Gly Gly Gly Ser Arg Tyr Thr Val Glu Leu Ala
    50                  55                  60
```

<210> SEQ ID NO 11
<211> LENGTH: 228
<212> TYPE: DNA
<213> ORGANISM: Artificial Sequence
<220> FEATURE:
<223> OTHER INFORMATION: Nucleic acid encoding CLP fusion protein
      comprising MMP and anti-inflammatory motifs

<400> SEQUENCE: 11

```
catatgtgcg gcccaaaagg acctaagggg cccaaaggcc ctaaaggccc accagggccc       60
ccaggtccgc caggacctcc agggaccccca ggcgatcctg ggatcccggg cgacccagga     120 ggaggggggcg gacgtccgct tggcttatgg gcggtgggg gtggacgcgg ctacactgtt      180
gagcttgctg ggggaggagg ccatcaccac caccaccact aaagcaga                  228
```

```
<210> SEQ ID NO 12
<211> LENGTH: 6
<212> TYPE: PRT
<213> ORGANISM: Artificial Sequence
<220> FEATURE:
<223> OTHER INFORMATION: RGDSPG Cell Adhesion Motif

<400> SEQUENCE: 12

Arg Gly Asp Ser Pro Gly
1               5

<210> SEQ ID NO 13
<211> LENGTH: 132
<212> TYPE: DNA
<213> ORGANISM: Artificial Sequence
<220> FEATURE:
<223> OTHER INFORMATION: Nucleic acid encoding CLP with RGDSPG motif

<400> SEQUENCE: 13
tgtggtccca agggccctaa agggccgaaa ggacctaagg gtcccctgg gccgccggga      60 cccctgggc accgggtga cccaggcgat ccagggatc caggcgatcc aggacgcggc      120
gattcgccgg ga                                                        132

<210> SEQ ID NO 14
<211> LENGTH: 5
<212> TYPE: PRT
<213> ORGANISM: Artificial Sequence
<220> FEATURE:
<223> OTHER INFORMATION: IKVAV Cell Adhesion Motif

<400> SEQUENCE: 14

Ile Lys Val Ala Val
1               5

<210> SEQ ID NO 15
<211> LENGTH: 129
<212> TYPE: DNA
<213> ORGANISM: Artificial Sequence
<220> FEATURE:
<223> OTHER INFORMATION: Nucleic acid encoding CLP with IKVAV motif

<400> SEQUENCE: 15
tgtggaccta aaggtcccaa gggtccaaag gggcctaaag gccccctgg tccgcccgga      60 ccgccaggac cacctggcga tcctggggac ccgggtgatc caggagaccc gggcattaaa    120
gtggcagtt                                                            129
```

COLLAGEN AND COLLAGEN LIKE PEPTIDE BASED HYRDOGELS, CORNEAL IMPLANTS, FILLER GLUE AND USES THEREOF

CROSS-REFERENCE TO RELATED APPLICATION

The present application claims priority from U.S. Provisional Patent Application No. 62/407,650 filed on Oct. 13, 2016 and PCT Patent Application No. PCT/IB2017/056342 filed on Oct. 13, 2017, of which the entire contents of both applications are hereby incorporated by reference.

FIELD OF INVENTION

The present invention relates to collagen and modified collagen-like peptides crosslinked using DMTMM as a crosslinker. The invention also relates to methods of preparing hydrogels, corneal implants and filler glue comprising collagen and collagen-like peptides crosslinked with DMTMM.

BACKGROUND

The cornea is the transparent covering and the main refractive element of the eye. It is responsible for transmission of light to the retina. The human cornea is composed of three primary layers, an outermost epithelium layer, a middle stroma containing keratocytes and an innermost single layer of endothelial cells.

One of the major causes of blindness worldwide is corneal diseases. The diseases lead to loss of corneal transparency and subsequently deteriorates the vision. There are a wide variety of infectious and inflammatory eye diseases that cause corneal scarring and may result in total blindness. Microbial attack is a common cause of corneal disease.

The most widely accepted treatment for corneal blindness is transplantation of a full thickness healthy donor cornea after removal of the damaged tissue. The process is termed as penetrating keratoplasty (PK). Unfortunately, the approach of penetrating keratoplasty suffers from several shortcomings due to the following reasons: —
  The supply of donor tissue is substantially less than the demand for transplantation that has resulted in 12.7 million untreated patients worldwide as reported in 2016, with an additional 1.5 million new patients every year.
  Donor cornea is often rejected in a large proportion of patients due to reasons such as autoimmune situations, chemical burns, and infections.
  Survival rate of corneal grafts decreases over time.
  Donor-cornea derived infection such as HSV is another serious complication associated with transplantation of human donor corneas. Donor corneas should be screened which is an expensive procedure, with processing fees in the USA around 2.5-3.5 thousand US dollars per cornea.
  There has been a long history of research into the development of alternatives to human corneas with both artificial as well as natural alternatives. Xenograft transplantation using corneas from pigs and sheep have been tried. But the said approach suffers from many disadvantages such as immune rejections as well as cross-species diseases due to transmission of pathogens.
  Decellularized organs have been studied to evaluate their potential as grafts in same or cross-species due to their ability to retain the native extra-cellular matrix of the target organ. But, decellularized corneas also have shortcomings due to incompatibility and rejections.

Artificial corneas known as keratoprostheses (KPro's) have been in development for over 200 years. Artificial corneas utilizing quartz crystal implant, plastic optical core like poly (methyl methacrylate), poly (2-hydroxyethyl methacrylate) etc. have been used. But the use of such artificial corneas involves the need for lifetime antibiotics as well as immune suppression in a large proportion of patients. The retention rates of these artificial corneas are extremely less and more than half of such artificial corneas do not last beyond three years. Moreover, the patients are at risk of glaucoma, a very severe side effect that can result in blindness.

As collagen is the main component of the corneal extra-cellular matrix, artificial corneas made from collagen have garnered a lot of interest as alternatives to human donor corneas. The main source of collagen is extracted animal protein, although recombinantly produced collagen is now available. To give mechanical strength, enzymatic stability and feasibility for transplantation, collagen is cross-linked by different mechanisms.

Optically transparent and cell friendly corneal implants made from porcine and bovine collagen and transplanted into animal models exhibit immunogenic reaction. Animal-derived collagen comes from heterogeneous sources, and because of the different levels of processing and screening in each different source, great care needs to be taken due to the risk of transmitting diseases as well as provoking immune responses in the host.

The use of recombinant human collagen mitigates the heterogeneity and pathogen transmission issue. However, the production and purification of recombinant human collagen is an expensive process that makes the price of the artificial cornea unreachable to the neediest individuals. Therefore, an alternative that could replace recombinant human collagen with the same physicochemical and biological properties would be a huge advancement. Collagen-like peptides (CLP) or collagen mimetic peptides have been developed as functional alternatives of collagen.

Corneal implants based on collagen-like peptides crosslinked using various cross-linkers have been developed till date. N-(3-dimethylaminopropyl)-N'-ethylcarbodiimide (EDC) and N-hydroxysuccinimide (NHS) crosslinking system has been used for development of corneal implants. But the same has been found to be cytotoxic to the surrounding cells.

DMTMM has been used as a crosslinker in a wide variety of applications. But the use of the same for development of hydrogels and implants is not known. The usage of DMTMM as a crosslinker has allowed unprecedented advantages over the previously used crosslinkers. The advantages include improved mechanical properties, improved thermal properties and less cytotoxic effect.

In the prior art, collagen-like peptides having characteristics very similar to that of collagens have been developed. One such collagen-like peptide having 36 amino acid has been used as a base peptide for the present invention, which is modified to impart mechanical strength and multifunctionality such as anti-inflammatory property and resistance to matrix metalloproteinases (MMP).

The implants based on collagen-like peptide crosslinked with DMTMM and containing the MMP cleavage motif and the anti-inflammation motifs is highly efficacious compared to the implants disclosed in the prior art.

The present invention thus contemplates to overcome the problems of the prior art to solve a long-standing problem of development of corneal implants with improved mechanical properties and less cytotoxic effect. Further, the approach used for development of this invention would make the improved implants more accessible and affordable to the 90% of the world's visually impaired who live in low-income nations.

Further, the invention may also be utilized for cosmetic purposes such as for correction of refractive errors, use as fillers for correcting previous laser eye surgery (PRK, LASIK, LASEK) or use as onlays, inlays and rings instead of laser eye surgery to correct vision. The filler glue can also be used as anti-aging tools to fill wrinkles.

SUMMARY OF THE INVENTION

The present invention relates to modified collagen-like peptides, wherein the peptides are operably fused to one or more functional peptide motifs having MMP cleavage site, anti-inflammatory properties and/or cell-adhesion sites.

Further, the invention discloses chemically modified collagen or collagen-like peptide-PEG (CLP-PEG) conjugate. The invention also relates to CLP-PEG conjugate which have been crosslinked into a network using 4-(4,6-Dimethoxy-1,3,5-triazin-2-yl)-4-methylmorpholinium chloride (DMTMM) as a crosslinker.

The invention discloses hydrogels comprising CLP-PEG conjugate crosslinked with DMTMM. Further, the hydrogel contains stem cells or a second layer of anti-inflammatory biopolymer.

The invention also relates to a method of preparing the hydrogel using CLP-PEG conjugate containing fibrinogen crosslinked with a crosslinking agent, preferably 4-(4,6-Dimethoxy-1,3,5-triazin-2-yl)-4-methylmorpholinium chloride (DMTMM). CLP-PEG hydrogel is in the form implant or filler glue.

Further, the invention relates to method of treatment using the hydrogel which includes pre-application of thrombin to the corneal defect. The CLP-PEG containing fibrinogen is mixed with DMTMM and dispensed into the cavity of the corneal defect. The thrombin reacts with the fibrinogen to form fibrin to result in a hydrogel.

The invention also relates to method of manufacturing corneal implants by preparation of a hydrogel and molding the implants as cornea shaped implants in a humidified chamber in an inert or non-oxidizing atmosphere.

BRIEF DESCRIPTION OF SEQUENCE LISTINGS

Figure 1:
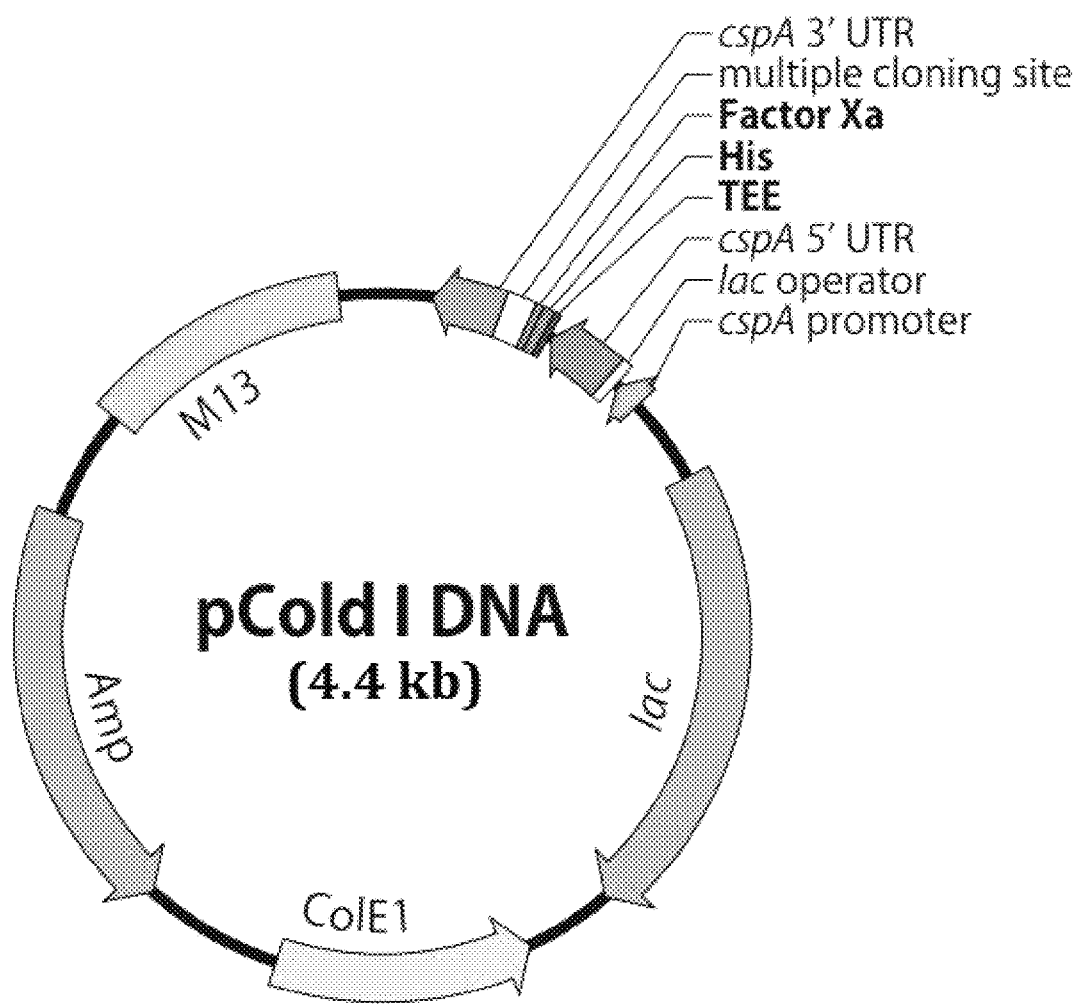
FIG. 1 depicts the vector map of the pCOLDI vector used for recombinant production of collagen like peptides.

SEQ ID NO:1 is the nucleic acid sequence of a *Pichia pistoris* template vector (pPink-aMF-COL mimic-His-P4H-HC) comprising 10 repeats of the nucleic acid sequence encoding the 38-amino acid CLP.

SEQ ID NO:2 is the nucleic acid sequence of the forward primer used for cloning.

SEQ ID NO:3 is the nucleic acid sequence of the reverse primer used for cloning.

SEQ ID NO:4 is the nucleic acid sequence encoding the 38-amino acid sequence used for preparation of CLP.

SEQ ID NO:5 is the 38-amino acid long polypeptide used as a base for preparation of CLP with added functional motifs. This sequence comprises of a previously disclosed 36-amino acid sequence to which a glycine and a cysteine residue has been added.

SEQ ID NO:6 is a Matrix-metalloproteinases (MMP) cleavage motif which is functionally fused to the peptide comprising the amino acid sequence of SEQ ID NO:5.

SEQ ID NO:7 is the nucleic acid encoding a CLP-MMP polypeptide, wherein the MMP cleavage motif is functionally fused to the polypeptide given in SEQ ID NO:5.

SEQ ID NO:8 is an anti-inflammatory motif (RYTVELA) which is functionally fused to the peptide comprising the amino acid sequence of SEQ ID NO:5.

SEQ ID NO: 9 is the nucleic acid encoding CLP-RYTVELA polypeptide, wherein the anti-inflammatory motif is functionally fused to the peptide comprising the amino acid sequence of SEQ ID NO:5.

SEQ ID NO: 10 is a polypeptide comprising CLP fused to both the MMP cleavage motif as well as the anti-inflammatory motif (RYTVELA).

SEQ ID NO:11 is the nucleic acid encoding polypeptide of SEQ ID NO:10.

SEQ ID NO:12 is a cell adhesion peptide motif RGDSPG (from fibronectin), referred to as "RGDSPG" or "RGD" herein, which is functionally fused to the peptide comprising the amino acid sequence of SEQ ID NO:5.

SEQ ID NO:13 is the nucleic acid encoding CLP-RGD-SPG polypeptide, wherein the cell adhesion peptide motif is functionally fused to the peptide comprising the amino acid sequence of SEQ ID NO:5.

SEQ ID NO:14 is a cell adhesion peptide motif IKVAV (from laminin) which is functionally fused to the peptide comprising the amino acid sequence of SEQ ID NO:5.

SEQ ID NO:15 is the nucleic acid encoding CLP-IKVAV polypeptide, wherein the cell adhesion peptide motif is functionally fused to the peptide comprising the amino acid sequence of SEQ ID NO:5.

Definitions

Unless defined otherwise, all technical and scientific terms used herein have the same meaning as commonly understood by one of ordinary skill in the art to which the methods belong. Although any methods and compositions similar or equivalent to those described herein can also be used in the practice or testing of the methods and compositions, representative illustrative methods and compositions are now described.

Where a range of values is provided, it is understood that each intervening value between the upper and lower limit of that range and any other stated or intervening value in that stated range, is encompassed within by the methods and compositions. The upper and lower limits of these smaller ranges may independently be included in the smaller ranges and are also encompassed within by the methods and compositions, subject to any specifically excluded limit in the stated range. Where the stated range includes one or both of the limits, ranges excluding either or both of those included limits are also included in the methods and compositions.

It is appreciated that certain features of the methods, which are, for clarity, described in the context of separate embodiments, may also be provided in combination in a single embodiment. Conversely, various features of the methods and compositions, which are, for brevity, described in the context of a single embodiment, may also be provided separately or in any suitable sub-combination. It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only"

and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other embodiments without departing from the scope or spirit of the present methods. Any recited method can be carried out in the order of events recited or in any other order that is logically possible.

The term "collagen" refers to the principal protein of connective tissue having a high tensile strength and found in most multicellular organisms. The term as used herein refers to all forms of collagen from diverse sources which can be used as starting materials, including but not limited to, recombinantly produced collagen, collagen extracted from naturally occurring sources, processed, or otherwise modified for preparation of hydrogels, implants or filler glue.

The term "collagen-like peptide" or "CLP" refers to any peptide which is a structural or functional equivalent of collagen. The CLP may further contain functional peptide motifs, which include but are not limited to, anti-inflammatory motif, MMP cleavage motif or cell adhesion motif.

The term "collagen-like peptide-PEG" or "CLP-PEG" or "conjugated-CLP" refers to any collagen-like peptide conjugated to polyethylene glycol, which includes but is not limited to, polyethylene glycols with molecular weight ranging 10-40 kDa, having 4-8 arms and having hexaglycerol or pentaerythritol core.

The term "hydrogel" means a gel comprising collagen-PEG or collagen-like peptide conjugate crosslinked into a network using a suitable crosslinker, which includes but is not limited to, DMTMM. The dispersion medium is any suitable solvent.

The term "corneal implant" refers to any material which may be applied to or comes in contact with the cornea of a subject. The corneal implant may comprise of a hydrogel comprising collagen or collagen like peptide crosslinked into a network using a suitable crosslinker, which includes but is not limited to, DMTMM. The implant may further comprise second network of functional polymers and may be used for delivery of cells.

The term "filler glue" or "filler" or "filler-glue" as used herein is intended to include hydrogels comprising collagen-PEG or collagen-like peptide conjugate crosslinked into a network using a suitable crosslinker and additionally comprises one or more component, which includes but is not limited to, peptide, glycoproteins, sealant, adhesives, additives etc. such as fibrinogen.

The term "stem cell" represents a generic group of undifferentiated cells that possess the capacity for self-renewal while retaining varying potentials to form differentiated cells and tissues. Stem cells can be pluripotent or multipotent. A pluripotent stem cell is a cell that has the ability to form all tissues found in an intact organism although the pluripotent stem cell cannot form an intact organism. Furthermore, it is known that human somatic cells can be re-programmed to an undifferentiated state similar to an embryonic stem cell. The term includes, but is not limited to, corneal stem cells.

The terms "polypeptide", "peptide" and "protein" are used interchangeably herein to refer to two or more amino acid residues joined to each other by peptide bonds or modified peptide bonds. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer. "Polypeptide" refers to both short chains, commonly referred to as peptides, oligopeptides or oligomers, and to longer chains, generally referred to as proteins. Polypeptides may contain amino acids other than the 20 gene-encoded amino acids. Likewise, "protein" refers to at least two covalently attached amino acids, which includes proteins, polypeptides, oligopeptides and peptides. A protein may be made up of naturally occurring amino acids and peptide bonds, or synthetic peptidomimetic structures. Thus "amino acid", or "peptide residue", as used herein means both naturally occurring and synthetic amino acids. "Amino acid" residues such as proline and hydroxyproline. The side chains may be in either the (R) or the (S) configuration.

DETAILED DESCRIPTION OF THE INVENTION

The present invention discloses modified collagen-like peptides prepared by adding one or more functional peptide motifs to a previously disclosed 36-amino acid peptide. Peptide motifs having proteolytic cleavage sites, anti-inflammatory effects and/or cell adhesion motifs are added to the amino acid sequence in this invention. Further, a glycine and a cysteine residue has been added to the peptide which allows covalent attachment of polyethylene glycol (PEG) to form a robust hydrogel.

Collagen or the collagen-like peptides crosslinked with DMTMM are used in preparing hydrogels and corneal implants and filler glue for treatment of corneal and defects and diseases.

The invention contemplates a multidimensional approach in development of highly efficacious corneal implants comprising collagen or collagen like peptides crosslinked with DMTMM. The hydrogels developed with collagen or collagen-like peptides crosslinked with DMTMM was found to be more effective and less cytotoxic than previously used EDC/NHS crosslinking system.

Efficacy of DMTMM Over Commonly Used Crosslinker

For the first time, DMTMM has been used as a crosslinker for development of collagen and collagen-like peptide based hydrogels, implants and filler glue. The inventors have established that DMTMM is a superior crosslinker as compared to existing crosslinkers such as EDC/NHS and N-Cyclohexyl-N'-(2-morpholinoethyl) carbodiimide metho-p-toluenesulfonate (CMC).

This inventive approach has led to the development of highly efficacious and robust hydrogels characterized by the following properties: —
  a. superior mechanical properties as evidenced by the oscillatory rheology studies
  b. improved suturability of the implants
  c. lesser cytotoxicity as evidenced by the human corneal epithelial cell culture studies performed with different crosslinkers and no long term cytotoxic effect
  d. increased integrity of the hydrogels over a long period as evidenced by the FTIR spectroscopic study
  e. superior anti-scarring properties
  f. increased induction of extracellular vesicle production Further the hydrogels developed in this invention have cosmetic uses as well such as the ability to correct refractive errors, use as fillers for correcting previous laser eye surgery (PRK, LASIK, LASEK) or use as onlays, inlays and rings instead of laser eye surgery to correct vision. The filler glue can also be used as anti-aging tools to fill wrinkles.

The invention also relates to methods of manufacturing hydrogels, corneal implants and filler glue comprising collagen or collagen-like peptides crosslinked with DMTMM.

Further, the invention also relates to method of treating corneal defects using hydrogels developed in this invention and a collagen based ab interno patch. The invention also reveals a kit comprising collagen based ab interno patch and the filler glue.

Before the collagen-like peptides, conjugates, hydrogels, implants, filler glue and methods of the present disclosure are described in greater detail, it is to be understood that the invention is not limited to particular embodiments and may vary. It is also to be understood that the terminology used herein is for the purpose of describing particular embodiments only, and is not intended to be limiting, since the scope of the methods and compositions will be limited only by the appended claims.

Aspects of the present invention relates to modified collagen like peptides which were designed using a 36-amino acid peptide sequence as a base. Functional motifs were added to this base peptide sequence in order to improve the functionality and therapeutic efficacy of the hydrogels based on these collagen-like peptides. Glycine and cysteine were added to allow covalent attachment with an 8-armed polyethylene glycol maleimide (PEG) and form a robust hydrogel. The functional motifs added to the base CLP included a MMP cleavage motif, an anti-inflammatory motif and cell adhesion motifs.

To impart resistance to matrix metalloproteinases (MMP), a MMP cleavage motif is added to stop the degradation of extracellular matrix proteins.

The collagen-like peptides developed in this invention contains MMP cleavage motif. Matrix-metalloproteinases (MMPs), also referred to as matrixins are a family of approximately 24 human zinc-containing endopeptidases that are capable of degrading components of the ECM and many other proteins. MMPs are overexpressed in a variety of pathological conditions, such as arthritic diseases, cancer and inflammation.

Compositions comprising a MMP cleavage motif are used to cleave MMPs at inflammation sites. Cell adhesion motifs like RGDSPG (from fibronectin) and IKVAV (from laminin) was added to enhance corneal epithelial cell proliferation and differentiation as well as neurite outgrowth.

Another aspect of the invention relates to recombinant production of collagen-like peptide. Recombinant production of collagen-like peptides provides impeccable high yields and thus resulting in managing the higher purities required at lower expenses.

In the present invention, the nucleic acids encoding the modified collagen like peptides are cloned into an expression vector for recombinant expression. In a preferred embodiment, the vector is a pCOLDI expression vectors.

The nucleic acids are cloned into the expression vector using the restriction sites and appropriate forward and reverse primers. In a preferred embodiment, the restriction sites are NdeI and XbaI.

For post-translational modification of proline residues to hydroxyproline, an expression vector encoding prolyl 4-hydroxylase is transformed along with the vector encoding the collagen like peptides. In a preferred embodiment, the vector used for encoding prolyl 4-hydroxylase is a pET vector.

A suitable host cell for expressing the recombinant collagen like peptides is used. In a preferred embodiment, the host cell used is $E.$ $coli$ BL-21(DE3) strain. In the preferred embodiment, the host cells used for production of recombinant proteins which are endotoxin-free.

For recombinant expression of CLPs, pre-cultured bacteria are selected against an antibiotic. In a preferred embodiment, the antibiotic is ampicillin.

The promoter present in the host is an inducible promoter. In a preferred embodiment, the promoter is IPTG.

The recombinant host cells are harvested by centrifugation and subjected to lysis for recovery of recombinant proteins. In a preferred embodiment, lysis is performed by sonication.

The collagen-like polypeptides are further purified using a suitable purification system. In a preferred embodiment Ni-NTI columns that specifically bind the Histidine tag attached to the N-terminus of CLP are used for purification.

The recombinantly expressed proteins which do not trigger endotoxic response in human cells and are used for preparation of hydrogels and implants.

Alternatively, the peptides are synthesized using a peptide synthesizer.

Further aspects of the invention deal with preparation of collagen or CLP-PEG hydrogel crosslinked into a network using DMTMM. Further, implants and filler glue using the hydrogel are prepared. For preparation of the hydrogel, the collagen or recombinantly produced collagen-like peptides are conjugated with polyethylene glycols with molecular weight ranging 10-40 kDa, having 4-8 arms and having hexaglycerol or pentaerythritol core. In a preferred embodiment, a 8-arm-PEG-maleimide having MW of 40 KDa and hexaglycerol core was used. The resultant CLP-PEG conjugate is subjected to a three-stage filtration process. In a preferred embodiment, the three-stage filtration process includes using a P3 sintered glass funnel, a 0.45 µm sterile filter and then purification by dialysis against water 12-14 KDa molecular weight cut-off regenerative cellulose dialysis membrane. The purified solution is finally lyophilized.

In a first embodiment, for preparation of the hydrogel, solution of CLP-PEGs in water is crosslinked using a suitable crosslinker. In a preferred embodiment, 15% (w/w) solution of CLP-PEGs in water is prepared and a 2-(N-morpholino) ethanesulfonic acid (IVIES) is added as a buffer. The crosslinker in the preferred embodiment is 4-(4,6-Dimethoxy-1,3,5-triazin-2-yl)-4-methylmorpholinium chloride (DMTMM).

In another embodiment, fibrinogen is mixed with CLP-PEG and then DMTMM is added for preparing the hydrogels. Thrombin is pre-applied to the corneal defect and when it comes in contact with fibrinogen of the hydrogel reacts to convert into fibrin, which is a superior filler glue.

For preparation of the implant, the hydrogel is moulded as cornea-shaped implants and cured overnight in a humidified chamber under an inert or non-oxidizing atmosphere. In a preferred embodiment, the inert or non-oxidizing atmosphere is nitrogen atmosphere.

For preparation of the CLP-PEG filler glue, the CLP-PEG conjugate is dissolved in deionised water. The resultant solution behaves as a liquid at 37° C. and is injectable. Optionally, fibrinogen can be added to this solution. Addition of DMTMM while cooling the 15% (w/w) solution of CLP-PEG from 37° C. to 25° C. is a preferred mode of preparing the filler glue.

Another aspect of the present invention relates to modified implants with anti-inflammatory biopolymer, small drugs and pre-loaded stem cells. The slow gelling kinetics of the hydrogel allows the homogeneous incorporation of a second network of anti-inflammatory and anti-fouling biopolymer. In a preferred embodiment, the anti-inflammatory and anti-fouling biopolymer is 2-methacryloyloxyethyl phosphorylcholine network (MPC). CLP-MPC implants are suitable to be used as implants for corneas with severe pathological conditions such as chemical burns, severe infections, autoimmune conditions etc. The slower gelling kinetics also allows the covalent attachment of various small molecule drugs such as vancomycin.

Yet another aspect of the present invention relates to preparation of collagen or CLP-based implant with pre-loaded stem cells for stem cell delivery to patients whose own endogenous stem cells are depleted. In a preferred embodiment, DeltaNp63 positive corneal limbal epithelial cells were grown on the implants and it was found that the implant supports the proliferation of the stem cells.

Further aspects of the present invention relate to characterization of the developed implants, which includes mechanical characterization, thermal characterization and cytotoxic characterization.

For mechanical characterization, oscillatory rheology studies were performed on these hydrogels and implants. The results depict that the implants have a much higher storage modulus and a much lower tangent loss than previously disclosed implants.

For thermal characterization, differential scanning calorimetric analysis was done which revealed that glass transition temperature of the hydrogels prepared with various equivalents of DMTMM matched the glass transition temperature of the human cornea.

Further cytotoxic characterization was performed by comparing implants prepared using different crosslinkers for growth of human corneal epithelial cells on the implants. For the comparison, the HCEC were seeded onto tissue culture plates and the effects of DMTMM and EDC/NHS crosslinking systems were compared for their effects on immortalized human corneal epithelial cells.

In a further aspect, the long-term toxicity of DMTMM on HCEC was tested. HCECs were incubated with DMTMM and was cultured for up to 7 days. Staining was done to check the viability of the cells.

In yet another aspect, the thickness of cornea was measured at different times before and after grafting the implants in New Zealand white male rabbits.

In other aspects of the invention, the suturability of the implants, anti-scarring properties, induction of extracellular vesicle production and stability of the implants over a long period of time are exhibited.

In another aspect of the invention, it has been shown that the suturability of the implants tested on excused pig eyes were found to withstand multiple interrupted sutures with little breaks.

In yet another aspect of the invention, the long-term integrity of the sample was studied using FTIR Spectroscopy. Samples were subjected to a wave-scan ranging 650-4000 $cm^{-1}$ and no significant differences in the spectra could be found between samples indicating the integrity of the implants over the storage duration of 14 months.

In yet another aspect, the anti-scarring properties of the implants were tested. The in vitro culture of primary dermal fibroblasts on the implants shows the ability of CLP implants to be potentially used as regeneration scaffolds or templates, preformed or in situ cured, to have an anti-scarring effect.

In yet another aspect, the ability of the implants to induce extracellular vesicle production was tested. Mini-pig neo corneas were investigated to characterize the exosomes and immunohistochemistry performed on sections of implanted with CLP-PEG and RHCIII-MPC showed differential staining for CD9 marker for exosomes, and Rab-7, a marker for endosomes. It was shown that CLP-PEG implants in the cornea promotes regeneration of extracellular vesicles.

In a further aspect, a method of treatment of corneal and defects and diseases is exhibited. Perforations were performed on the cornea and standardized corneal defects were made. The defects were then sealed by patching using A) conventional ab externo patching with cyanoacrylate glue B) a collagen hydrogel based ab interno patch only; C) a collagen hydrogel ab interno patch together with a CLP-PEG filler.

Further, bursting pressure was evaluated to show that the patching done using CLP-PEG-fibrinogen filler glue to show that it is the best possible method for sealing the corneal defects.

EXAMPLES

Example 1: Collagen Like Peptides

The collagen-like peptides were designed using a 36-amino acid peptide, (Pro-Lys-Gly)$_4$(Pro-Hyp-Gly)$_4$(Asp-Hyp-Gly)$_4$ as a base. To this polypeptide sequence, a glycine and a cysteine were added to allow covalent attachment to an 8-armed polyethylene glycol maleimide (PEG) and form a robust hydrogel. Further peptide motifs were added to this which allowed the polypeptides to be multifunctional.

A *Pichia pistoris* template vector (pPink-aMF-COL mimic-His-P4H-HC) comprising 10 repeats of the nucleic acid sequence encoding the 38-amino acid CLP was used as a template vector. The nucleic acid sequence of the template vector is represented by SEQ ID NO:1.

Using a forward primer comprising the nucleic acid sequence of SEQ ID NO:2 and a reverse primer comprising the nucleic acid sequence of SEQ ID NO:3, one repeat of the nucleic acid encoding the 38-amino acid sequence was isolated. The nucleic acid sequence of this repeat is represented by SEQ ID NO:4.

This repeat fused with added functional motifs were cloned into a pCOLDI vector (Takara Bio Inc) using NdeI and XbaI restriction site. The forward primer and the reverse primers used are represented by SEQ ID NO: 2 and SEQ ID NO:3 respectively.

In the present invention, several polypeptides were synthesized using the 38-amino acid polypeptide as a base. The 38-amino acid polypeptide is represented by SEQ ID NO: 5.

A Matrix-metalloproteinases (MMP) cleavage motif was functionally fused to the peptide comprising the amino acid sequence of SEQ ID NO:5. The MMP motif is represented by SEQ ID NO:6 and the nucleic acid encoding the CLP-MMP polypeptide is represented by SEQ ID NO:7.

An anti-inflammatory motif (RYTVELA) was functionally fused to the peptide comprising the amino acid sequence of SEQ ID NO:5. The anti-inflammatory motif is represented by SEQ ID NO:8 and the nucleic acid encoding the CLP-MMP polypeptide is represented by SEQ ID NO:9.

Further, a nucleic acid encoding the CLP fused to both the MMP cleavage motif as well as the anti-inflammatory motif was designed. The fusion polypeptide is represented by SEQ ID NO:10 and the nucleic acid encoding the fusion polypeptide is represented by SEQ ID NO:11. The CLP as represented by SEQ ID NO:10 was used in all the experiments concerning the evaluation of implants, unless otherwise specified in the specific embodiments.

Further, the collagen-like peptides were modified to incorporate the cell adhesion peptide motifs RGDSPG (from fibronectin) and IKVAV (from laminin) into the peptide sequence.

The fusion polypeptide CLP-RGDSPG is represented by SEQ ID NO:12 and the nucleic acid encoding the fusion polypeptide is represented by SEQ ID NO:13.

The fusion polypeptide CLP-IKVAV is represented by SEQ ID NO:14 and the nucleic acid encoding the fusion polypeptide is represented by SEQ ID NO:15.

Example 2: Recombinant Production of Recombinant Collagen Like Peptides

The nucleic acids of Example 1 were cloned into pCOLDI expression vectors (Takara Bio Inc). The vector map of the expression vector pCOLDI is depicted in FIG. 1. The restriction sites used in the process were NdeI and XbaI. Further, the forward primer and the reverse primers used are represented by SEQ ID NO: 2 and SEQ ID NO:3 respectively.

For post-translational modification of proline residues to hydroxyproline, a pET vector comprising the nucleic acid encoding Prolyl 4-hydroxylase was used.

Both the expression vectors (pCOLDI and pET) were transformed into *E. coli* BL-21(DE3) strain. The *E. coli* BL-21(DE3) electrocompetent strain is sold under the tradename of CLEARCOLI®. The CLEARCOLI® BL21(DE3) bacterial cells were used for production of recombinant proteins which are endotoxin-free.

For recombinant expression of CLPs, 4-20 µL of pre-cultured bacteria selected against ampicillin solution were inoculated into 40 mL LB Miller medium with 100 µg/mL ampicillin and 0.5% glucose and grown for 16 h at 37° C. on a shaking board (150 rpm). After 16 hr, the bacteria culture was given to 1 L LB Miller with 100 µg/mL ampicillin and grown at 37° C. and 150 rpm shaking until the $OD_{600}$ was between 0.6-0.8.

IPTG was added to achieve a final concentration of 1.5 mM IPTG CLP protein culture. Bacteria were then grown at room temperature for 16 h on a shaking board (150 rpm).

The recombinant host cells were harvested by 20 min centrifugation (5000×g, at room temperature). The supernatants were discarded and pellets were stored at −20° C. Thereafter, the bacterial pellets were resuspended in 10 mL denaturing binding buffer (20 mM sodium phosphate dibasic, 0.5 M NaCl, 40 mM imidazole, 8 M urea (U5378, Sigma), pH 8.0) per 1 gm pellet and lysed by sonication.

The solution was sonicated at 4° C. for 60×10 s with 10 s break and a 45-min break between the first 30 and the last 30 pulses. Samples were then centrifuged for 2×20 min at 5000×g at 4° C. and supernatants were transferred to new tubes which were then stored at 4° C.

Example 3: Purification of Recombinant Collagen Like Peptides

The collagen-like polypeptides were purified using Ni-NTI columns that specifically bind the Histidine tag attached to the N-terminus of CLP.

Figure 2:
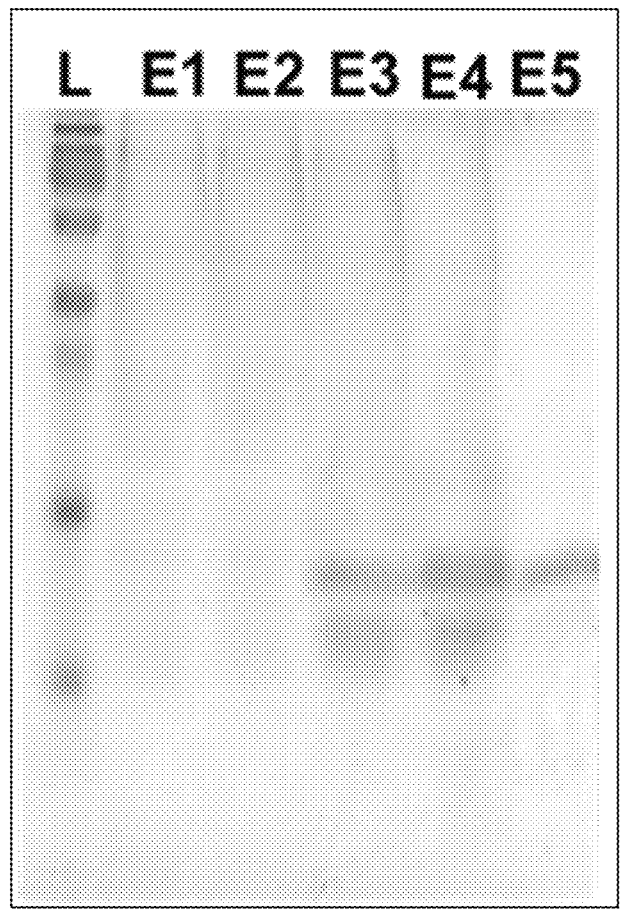
FIG. 2 shows recombinantly produced CLP shown as bands on an SDS-PAGE gel.

The Ni-NTA columns were equilibrated with 10-15 CV denaturing binding buffer, and supernatant of protein sample was applied. The column was washed with 3×2 mL denaturing binding buffer, and proteins eluted with 5 CV denaturing elution buffer (20 mM sodium phosphate dibasic, 0.5 M sodium chloride, 0.5 M imidazole, 8 M urea, pH 8.0). Samples were collected and analyzed using SDS PAGE. The recombinant CLPs were subjected to SDS-PAGE using standard protocol. The results of SDS-PAGE are depicted in FIG. 2. The E1-E5 of the SDS PAGE results depicts the eluent of CLP represented by SEQ ID NO:10. The His-tag polypeptides were visualized using 300 mM imidazole.

For dialysis, all the elutes with protein were collected and mixed in one 50 ml tube. The Slide-A-Lyzer-® Dialysis Cassette G2 (#87730, Thermo Scientific) was used according to the manufacturer's protocol for using a pipette. The native binding buffer from purifying the protein served as dialysis buffer, and dialysis was performed overnight at 4° C.

To further minimize the salt content of the dialyzed CLP protein solution, gel filtration was conducted using PD-10 Desalting columns with 8.3 mL SEPHADEX™ G-25 Medium (52-1308-00 BB, GE Healthcare) and the provided gravity protocol at room temperature. Elution was performed with 6 mL 1× phosphate buffered saline (PBS, P5368, Sigma) and eluates were kept on ice at 4° C.

CLP samples were entirely frozen in a falcon tube at −80° C. The cap was then replaced by parafilm and perforated with a syringe enabling liquid to evaporate. The tube was placed under vacuum until all liquid had evaporated.

Example 4: Preparation of CLP-PEG Conjugate

Recombinant collagen-like peptides as obtained in the previous example were used for the preparation of CLP-PEG conjugate. 8-arm-PEG-maleimide (MW 40 KDa, hexaglycerol core) was purchased from Creative PEG Works (Chapel Hill, N.C., USA).

20 mL of water was sparged with N2 for 20 minutes. To the sparged water, 8-Arm PEG-maleimide (770 mg, 18.7 µmol) was added until complete dissolution is achieved. CLPs (625 mg, 149.5 µmol, 8 molar equivalent w.r.t PEG) were added to the stirred solution as solid powder.

The reaction mixture was stirred for 20 min at 25° C. until the PEG is completely dissolved. The pH of the reaction mixture was adjusted to 4.5 by the dropwise addition of 2M NaOH and 30 mL of sparged water in three portions was further added to allow proper stirring. The reaction flask was covered in aluminium foil and allowed to stir for 5 days at 25° C. At the end of the $5^{th}$ day, additional 50 mL of water was added and the the pH of the reaction mixture was readjusted to 4.5.

The solution was then taken up into a 50-mL syringe and filtered through a 0.45 µM syringe filter. The filtered solution was then transferred to dialysis tubing having MWCO 12-14 kDa, preferably MWCO 14 kDa. The dialysis tubes containing the filtrate were then transferred to a 2 L beaker containing pH 4.5 water (pH adjusted through the dropwise addition of concentrated HCl and measured using a pH electrode). The beaker was stirred with a large magnetic stir bar and covered with aluminum foil. The dialysis water was exchanged twice daily for 7 days. The contents of the dialysis bags were then transferred to 50 mL Falcon tubes as 25 mL aliquots. The solutions were then frozen overnight in the −80° C. freezer. The Falcon tubes were then freeze-dried and the CLP-PEG conjugate was obtained as a cotton like solid. (Temp=−48° C. and Vacuum=90×$10^{-3}$ bar). This process took 5 days on the employed system.

For preparation of 10% (w/w) solution of CLP-PEG, 300 mg of CLP-PEG was added to the barrel of the sterile syringe. 2700 µL of water was added plunger of 10 mL sterile syringe to have a final concentration of 10% (w/w).

The syringe was sealed with parafilm and the CLP-PEG was allowed to reconstitute at room temperature for 2-3 weeks. For the reconstitution process, the mixture was stirred periodically with a spatula and heated in an incubator to 37° C. Once, the solution was completely resuspended, it was heated above its melting temperature, above 37° C. and centrifuged at 3000 rpm for 10 minutes. This process was repeated until all bubbles were removed from the syringe.

Figure 3:
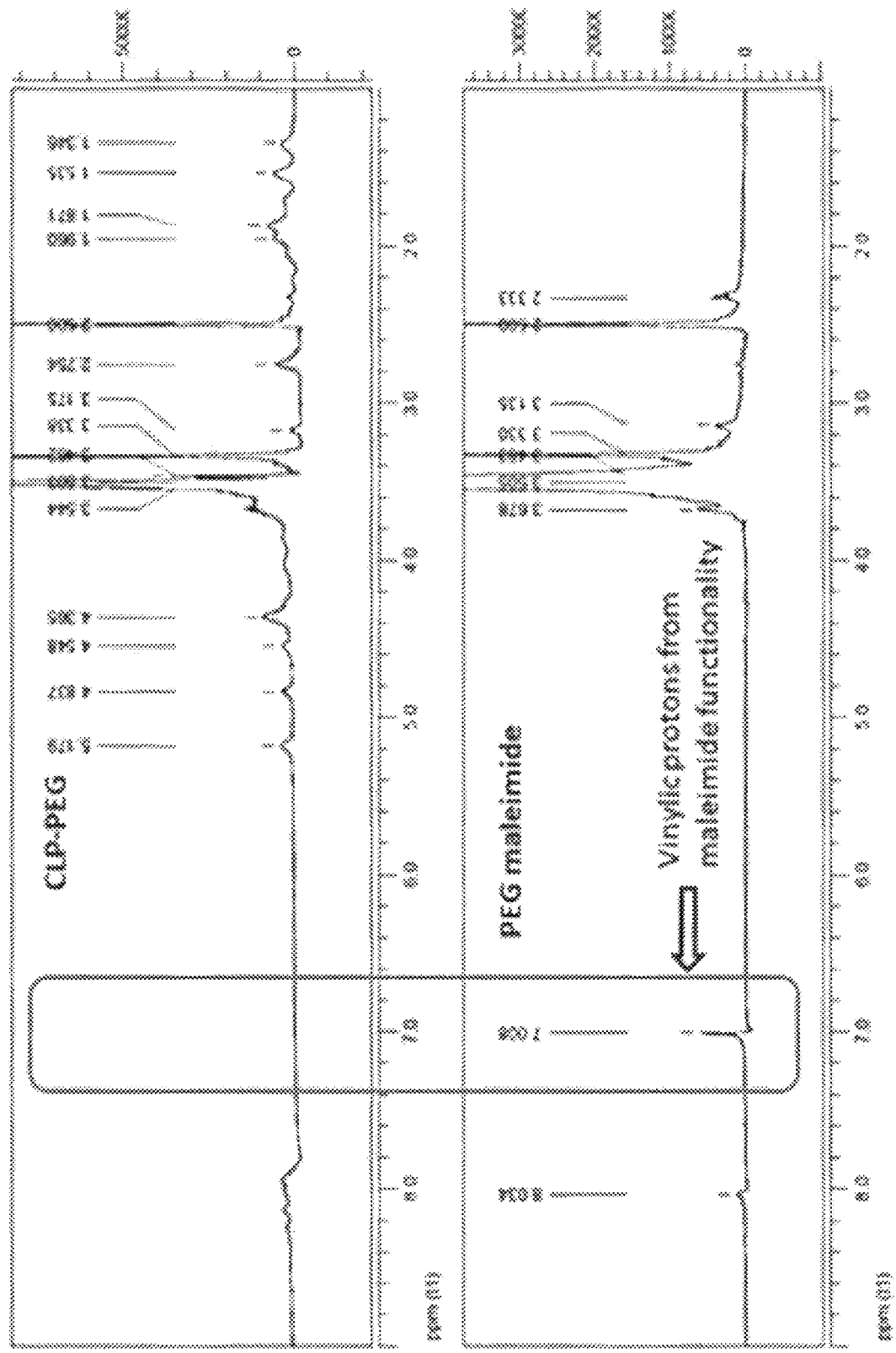
FIG. 3 depicts the results of comparison of $^1$H-NMR spectra of CLP-PEG (top) and 8-arm-PEG-maleimide (bottom) in DMSO-d6. The solvent peak at 2.5 δ ppm was used as internal standard. The successful conjugation of the CLP to the PEG-maleimide was confirmed by the complete disappearance of the vinylic proton peak at 7 δ ppm.

The CLP-PEG conjugate was characterised by $^1$H-NMR spectroscopy (Jeol 400 MHz NMR spectrometer, Joel Nordic AB, Sollentuna, Sweden) using DMSO-d6 as a solvent. The results of the spectroscopic analysis are depicted in FIG. 3.

The solvent peak at 2.5 δ ppm was used as internal standard. The successful conjugation of the CLP to the PEG-maleimide was confirmed by the complete disappearance of the vinylic proton peak at 7 δ ppm.

Example 5: Preparation of CLP-PEG Hydrogel and Implant

15% (w/w) solution of CLP-PEGs (32 lysines per CLP-PEG molecule) in water was prepared. 26 μl of 0.625M solution of 2-(N-morpholino) ethanesulfonic acid (MES) was added as a buffer.

The crosslinker used for the preparation of the hydrogel was 4-(4,6-Dimethoxy-1,3,5-triazin-2-yl)-4-methylmorpholinium chloride (DMTMM).

For preparation of the hydrogel, the crosslinker was taken at a concentration of one equivalent per lysine residue in CLP-PEG. The crosslinker was added as 10% solution in 0.625M MES.

The resulting mixture containing the CLP-PEG and the crosslinker was mixed thoroughly and moulded as cornea-shaped implants and cured overnight in a humidified chamber under nitrogen atmosphere. The final CLP-PEG concentration in this hydrogel was 9.8% (w/w).

Hydrogels and implants was also prepared using collagen crosslinked with DMTMM.

Example 6: Preparation of CLP-PEG Filler Glue

A thermo-assisted chemically crosslinked formulation was developed based on CLP-PEG using DMTMM chemistry.

For preparation of the CLP-PEG filler glue, the CLP-PEG conjugate was dissolved in deionised water (pH 7) at 15% (w/w) concentration. The resultant solution behaves as a liquid at 37° C. and is injectable. But, the solution sets as a gel when cooled to 25° C. due to the templated assembly of the CLPs. This sol-gel transition of CLP-PEG is reversible.

This sol-gel transition was made irreversible by adding a solution of DMTMM in 10 mM PBS to an end concentration of 4% (w/v) while cooling down the 15% (w/w) solution of CLP-PEG from 37° C. to 25° C. The hydrogel obtained is used as a filler glue.

DMTMM initiates amide bond formation between the side chain carboxylic acids and amines from the aspartic acid and lysine in CLP, respectively. This gel usually sets within 2 min.

Figure 4:
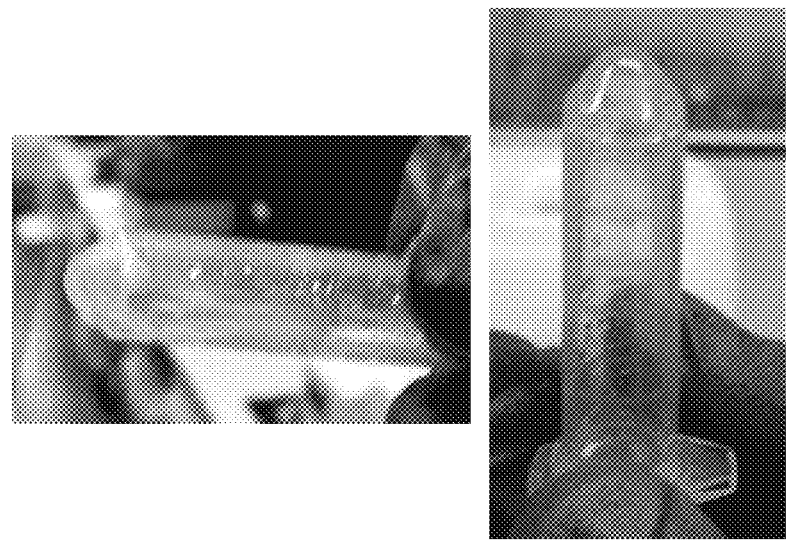
FIG. 4 shows thermo-assisted irreversible sol (left)-gel (right) transition using DMTMM crosslinking chemistry.

FIG. 4 depicts thermo-assisted irreversible sol (left)-gel (right) transition using DMTMM crosslinking chemistry.

Since the corneal surface temperature is around 34° C., it is possible to inject this material after mixing with DMTMM at 37° C. onto the corneal surface where the material undergoes irreversible in vivo/in cornea gelling due to the lower surface temperature of the cornea. The cornea is further cooled if necessary to facilitate this process.

Example 7: Preparation of Collagen-Based Ab Interno Patch

For preparation of collagen-based ab-interno patches, 10% (w/w) solution of porcine type I collagen (molecular weight 300 KDa, 114 lysines per collagen molecule, Nordic Biolabs AB, Stockholm, Sweden) in water was added to 200 μl of 0.625M solution of MES and loaded onto a syringe mixing system. Further, 12 μl of 2M NaOH was added to achieve a pH of 5.5.

The resulting solution was further mixed thoroughly with occasional cooling on ice. N-Hydroxysuccinimide (NHS) (0.4 equivalent with respect to the number of lysine in collagen) was added as a 10% solution in 0.625M MES and mixed thoroughly. It was followed by the addition of EDC (0.7 equivalent w.r.t the number of lysine in collagen) as a 5% solution in 0.625M MES. After addition of the EDC, the reaction mixture was mixed very quickly and moulded as a thin sheet of 100 μm thickness and cured overnight in a humidified chamber under nitrogen atmosphere. The final collagen concentration in the ab interno patch was 5.5% (w/w).

The collagen-based ab interno patch and the CLP-PEG filler glue as provided in Example 5 can be packed into a kit for clinical applications.

Example 8: Preparation of CLP-PEG Hydrogel with Fibrinogen

For enhancing the properties of CLP-PEG hydrogel and filler glue, fibrinogen was added. 300 mg of 10% CLP-PEG as prepared in Example 3 was used. 30 mg of fibrinogen (clottable protein-TISSEEL™ Kit) and 2700 μL of water was added to the barrel of the syringe to have a final concentration of 10% (w/w) CLP-PEG and 1% (w/w) fibrinogen.

The syringe was sealed with parafilm and the CLP-PEG and fibrinogen was allowed to reconstitute at room temperature for 2-3 weeks. To help the reconstitution process, the mixture was stirred periodically with a spatula and can also be heated in an incubator to 37° C. Once the solution was completely resuspended, it was heated above its melting temperature, i.e., 37° C. and centrifuge at 3000 rpm for 10 minutes. This process was repeated until all bubbles were removed from the syringe.

Examples 9: Preparation of CLP-PEG-Fibrinogen Filler Glue

The solution within the syringe containing 10% w/w CLP-PEG and 1% (w/w) fibrinogen behaves as a liquid (injectable) at temperatures above 37° C. but sets as a gel when cooled to 25° C. due to the templated assembly of the CLPs. However, this sol-gel transition is reversible. In order to make this sol-gel transition irreversible we add a solution of the crosslinker 4-(4,6-Dimethoxy-1,3,5-triazin-2-yl)-4-methylmorpholinium chloride (DMTMM) in 10 mM PBS to the mixture so that the final concentration of DMTMM is 2% w/w while cooling down the solution of CLP-PEG and fibrinogen from above 37° C. to 25° C.

For preparing the CLP-PEG-fibrin, the CLP-PEG/Fibrinogen mixture was heated for 5 minutes at 50° C. An appropriate amount of CLP-PEG/Fibrinogen mixture was transferred to a 2-mL glass syringe.

A T-piece system was primed with 10 mM PBS. The syringe containing the CLP-PEG/Fibrinogen mixture was attached to the T-piece system. The T-piece system was heated in a 50° C. incubator for 5 minutes. The solution was mixed 75 times. 10% (w/w) solution of DMTMM was prepared in 10 mM PBS. DMTMM solution was added to the Hamilton micro syringe through the addition port on the T-piece system. The solution was again mixed 75 times to obtain the hydrogel containing CLP-PEG-Fibrinogen glue.

The hydrogel was cast into 500 µM corneal molds for preparing implants. The jig was then used to tighten the molds. The molds/jig were then placed in a humidity chamber at room temperature for 24 hrs. The molds were then removed from the jigs and allowed to soak in water for 18 hrs. The implants were then demoulded and transferred to a sterile vial containing 10 mM PBS.

Example 10: Application of CLP-PEG-Fibrinogen Filler Glue

The application of CLP-PEG-Fibrinogen filler glue is done in combination with thrombin.

Thrombin was reconstituted at 250 U/mL by addition of 4 mL of 10 mM PBS to the vial of Thrombin (TISSEEL™ Kit). The solution was mixed at room temperature for 20 minutes prior to use. The solution can be aliquoted into several Eppendorf tubes and frozen for future use.

The thrombin is applied to the wound bed/intrastromal pocket. The filler glue is then applied to the wound. The thrombin converts fibrinogen to fibrin when combined with the CLP-PEG-Fibrinogen filler glue.

Figure 16:
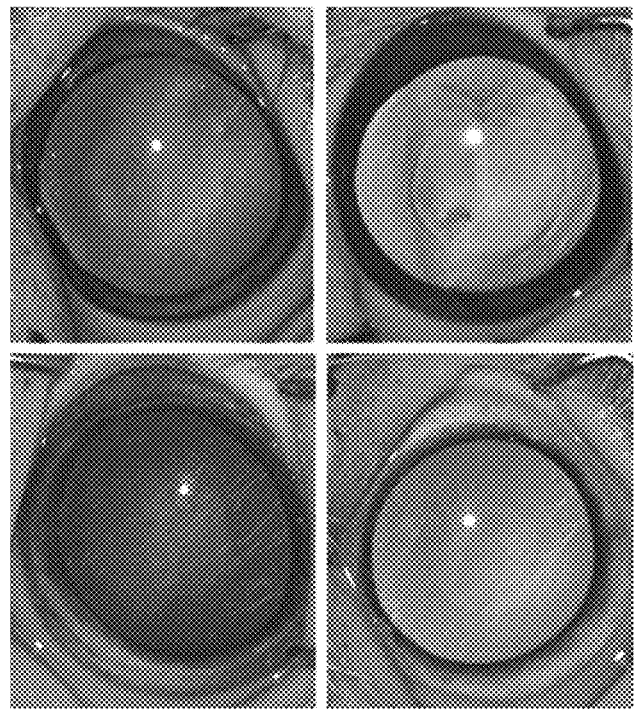
FIG. 16 shows all 8 operated animals at 12 months post-operation. Some blood vessels are seen in the eyes along with haze. Overall, the haze and vascular is slightly more prominent and even within the CLP-PEG group while the haziness in the MPC containing group is peripheral within the implant. Analyses of the collagen content showed that CLP-PEG implants had a higher overall content of collagens 1 and V than healthy unoperated corneas, while CLP-PEG-MPC implants had overall significantly less collagen. However, CLP-MPC showed a similar amount of high molecular weight, i.e. mature collagen fibrils as the healthy unoperated controls.
Figure 16:
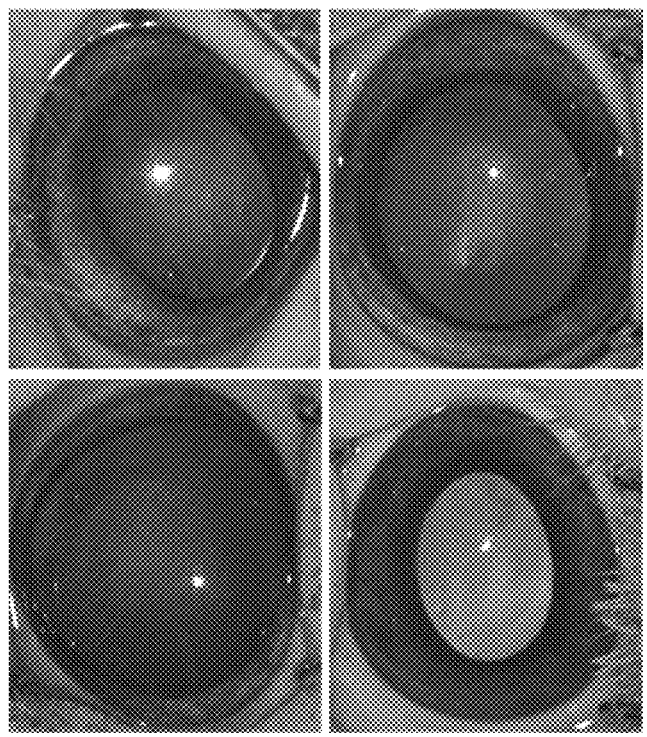
Figure 17:
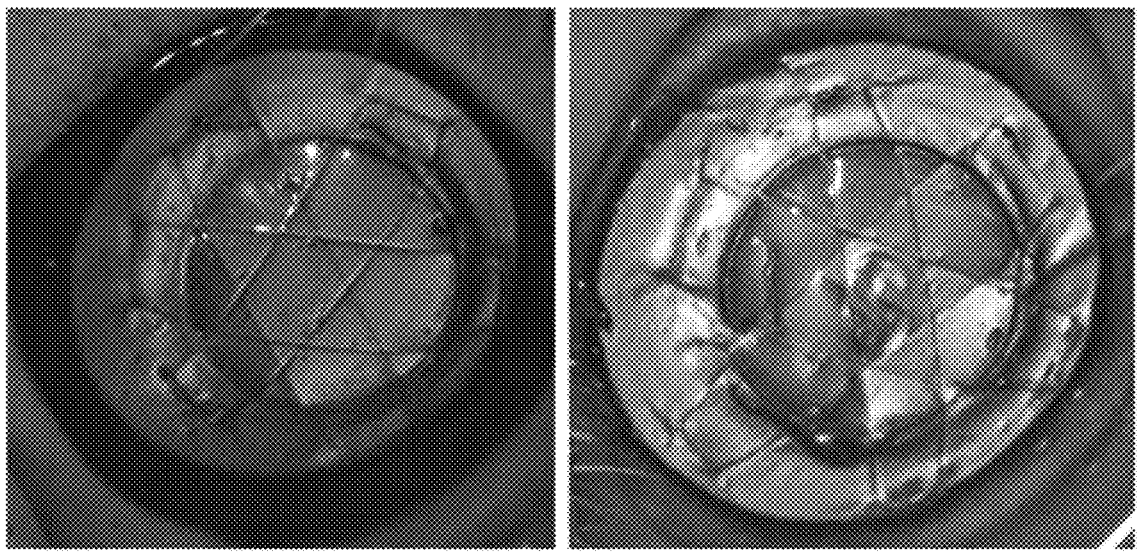
FIG. 17 depicts the CLP-PEG implant in the corneas of two representative mini-pigs immediately after surgery and at 5 weeks post-operation.
Figure 17:
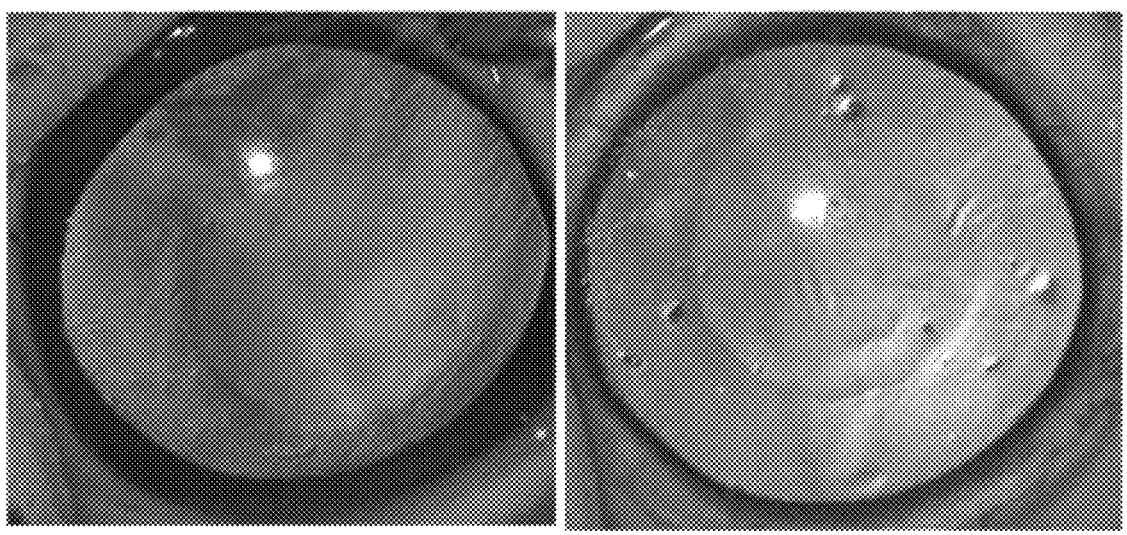

Example 11: Incorporation of a Second Network of Anti-Inflammatory Biopolymer and Attachment of Small Drug Molecule The hydrogel obtained in the Example 5 was used and the slow gelling kinetics allowed the homogeneous incorporation of a second network of anti-inflammatory and anti-fouling biopolymer of 2-methacryloyloxyethyl phosphorylcholine network (MPC). Stably integrated CLP-PEG-MPC implants are depicted in FIG. 16.

CLP-MPC implants are suitable for use as implants for corneas with severe pathological conditions such as chemical burns, severe infections, autoimmune conditions etc. The incorporation of a second layer has also allowed the covalent attachment of various small molecule drugs such as vancomycin. Further, various sustained drug release systems have been incorporated during fabrication of implants.

Example 12: CLP-Based Implant with Pre-Loaded Stem Cells

The CLP based implants crosslinked with DMTMM was tested for adverse effects. The cell proliferation data on DMTMM based implant is given in FIG. 7. The data depicted that DMTMM was non-cytotoxic to the stem cells.

The in vivo stem-cell delivery capabilities of the CLP-PEG implants were tested. DeltaNp63 corneal limbal epithelial cells were grown on the CLP-PEG implant and a RHC-MPC based implant was used as control.

Figure 5:
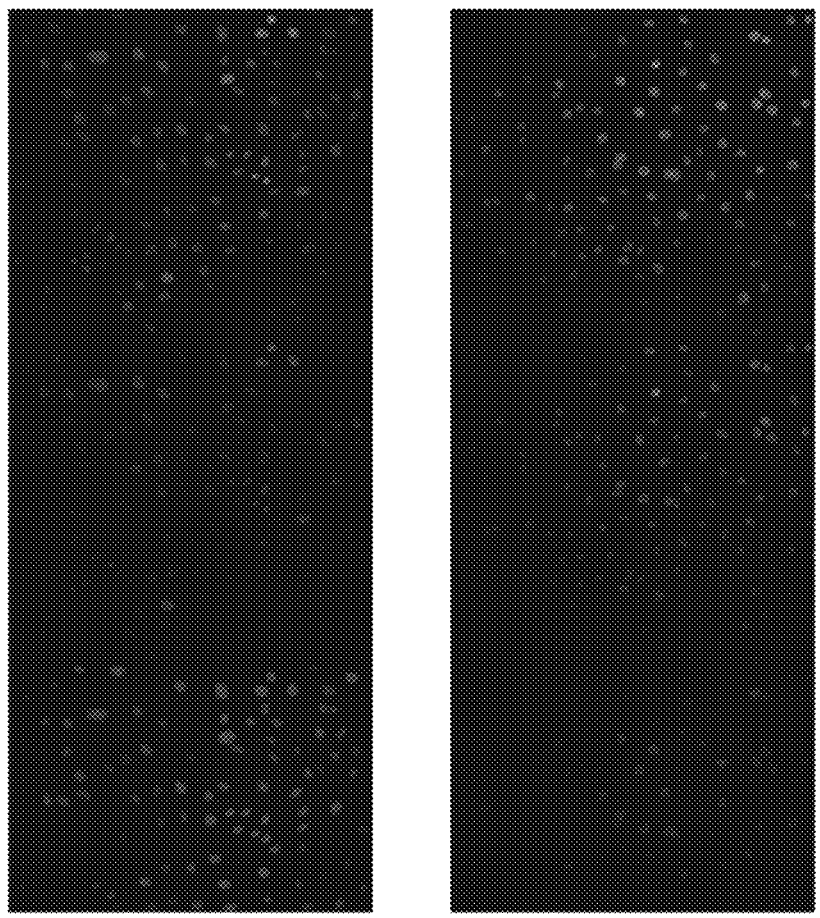
FIG. 5 shows primary corneal limbal stem cells on CLP-PEG and control RHC-MPC. Both support the proliferation of these stem cells, which are marked by the presence of DeltaNp63.

FIG. 5 shows the growth of DeltaNp63 positive corneal limbal epithelial cells, compared to cells grown on RHC. Primary corneal limbal stem cells on CLP-PEG and control RHC-MPC. Both support the proliferation of these stem cells, which are marked by the presence of DeltaNp63.

The CLP-PEG implants have potential to be used in incorporating stem cells for delivery to patients whose own endogenous stem cells are depleted.

Example 13: Mechanical Characterization of CLP-PEG Corneal Implant and Collagen-Based Ab Interno Patch Studies were conducted to characterize and compare the CLP-PEG implants of the present invention.

Various concentration of crosslinkers were used which resulted in hydrogels with various degree of resilience. The following hydrogels with N-Cyclohexyl-N'-(2-morpholinoethyl) carbodiimide metho-p-toluenesulfonate (CMC) and DMTMM as a crosslinker were prepared:

TABLE 1

Various concentration of crosslinkers used

| Sr. No. | Crosslinker used | Concentration |
| --- | --- | --- |
| 1 | CMC | 0.4 equivalent |
| 2 | DMTMM | 0.4 equivalent |
| 3 | DMTMM | 0.8 equivalent |
| 4 | DMTMM | 1 equivalent |
| 5 | DMTMM | 1.5 equivalent |

N-Cyclohexyl-N'-(2-morpholinoethyl) carbodiimide metho-p-toluenesulfonate (CMC) crosslinked hydrogels were stable only up to 20 Hz in a frequency sweep experiment whereas hydrogels crosslinked with various concentration of DMTMM were found to withstand up to 90 Hz of oscillation frequency.

Figure 6:
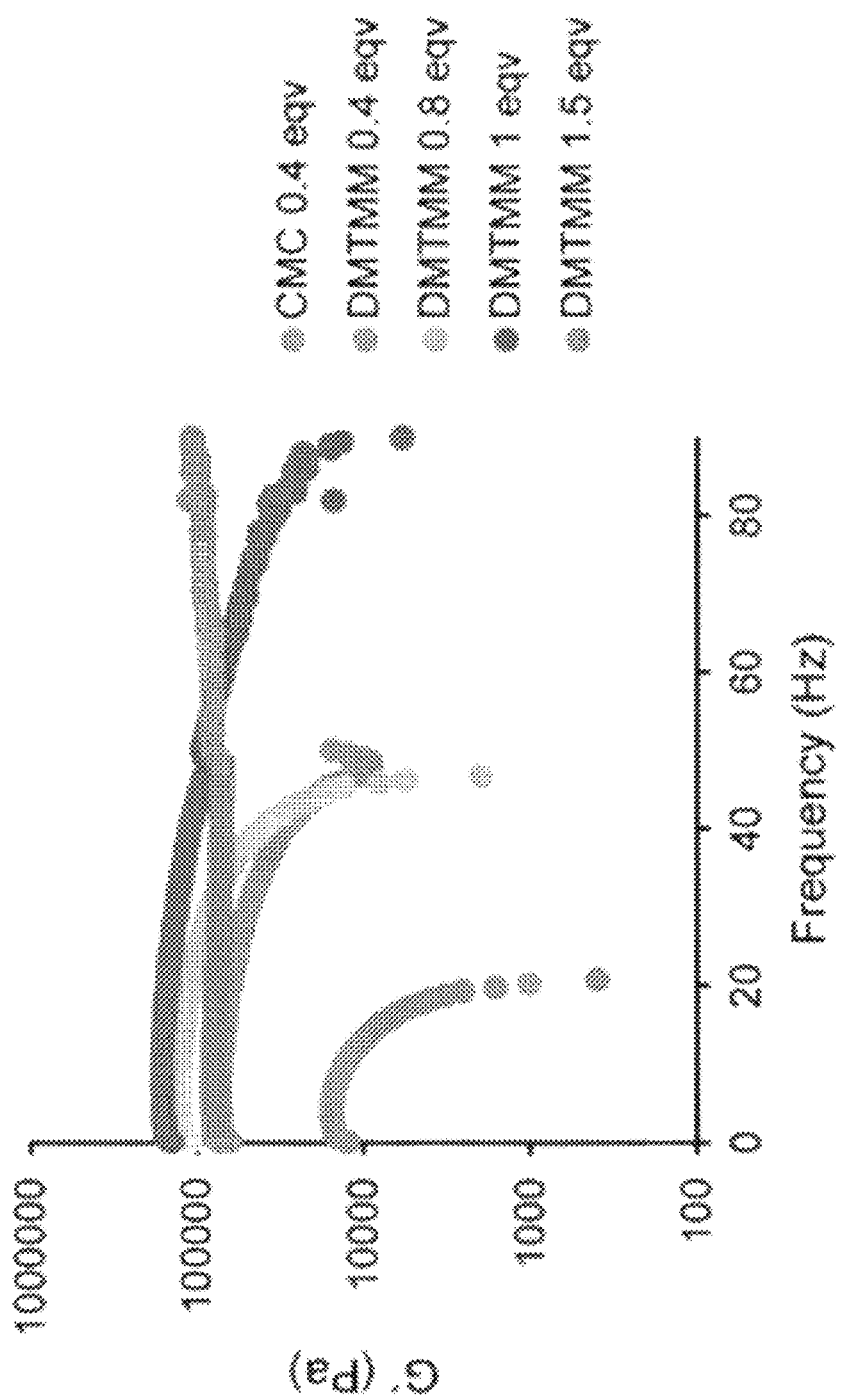
FIG. 6 shows the oscillatory rheology studies of DMTMM crosslinked collagen implants.

The results of the studies on oscillatory rheology of DMTMM crosslinked collagen implants are depicted in FIG. 6. The results show an unprecedented improvement in mechanical strength for collagen-based hydrogels crosslinked with DMTMM. The slower gelling kinetics of DMTMM allows very refined and homogeneous entanglement of polymers chains throughout the hydrogel which explains the very high resilience of these materials.

In another study, the mechanical properties of CLP-only implants were also evaluated. The physical integration of CLP-PEG hydrogels into host corneas were evaluated by implantation of hydrogels into rabbit corneas. The shear properties of the regenerated neo-corneas after 6-month post-operation were compared to that of the initial implants and healthy rabbit corneas using oscillatory rheology studies. The CLP-PEG implants have a much higher storage modulus and a much lower loss tangent than normal, healthy rabbit corneas as found from a frequency sweep measurement. The results indicate that the implants are much stiffer and less compliant.

The natural rabbit corneas suffer from relatively high loss tangent. The loss tangent was found to be in the range of 0.15-0.25 in case of both implanted corneas and un-operated healthy corneas, whereas that for the implants were found to be within 0.01-0.02.

Since there is an enormous difference in mechanical characteristics of the initial implant and the regenerated or healthy corneas and no significant differences between the operated and un-operated corneas for any given rabbit, it is concluded that the implants were stably integrated into the host tissue.

Figure 9:
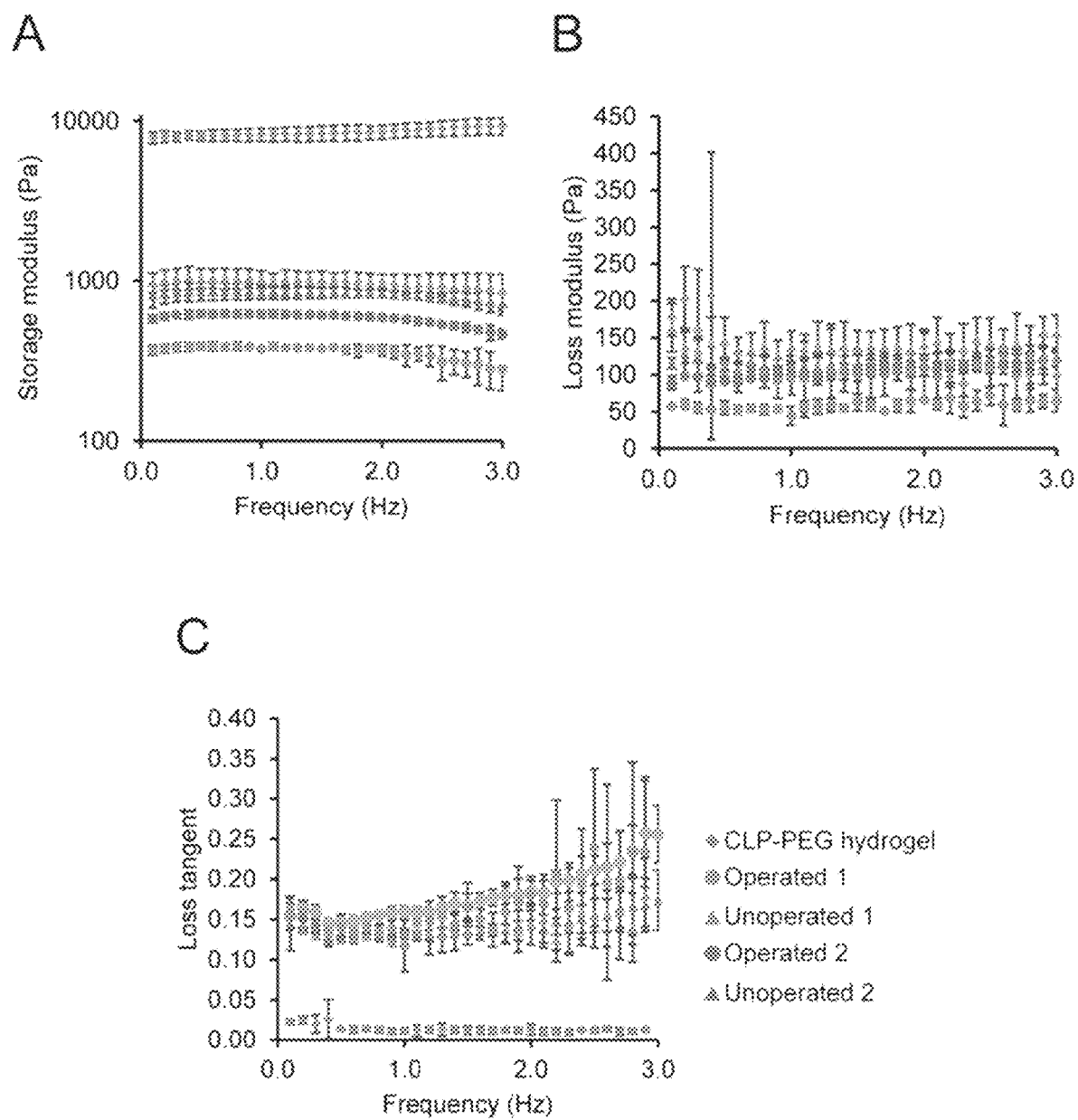
FIG. 9 depicts results of oscillatory rheology studies of operated and un-operated rabbit corneas and CLP-hydrogel implant; (a) storage modulus, (b) loss modulus and (c) loss tangent as a function of oscillation frequency at 0.27% shear strain amplitude.

The oscillatory rheology of operated and unoperated rabbit corneas and CLP-hydrogel implants are depicted in FIG. 9. The results depict the storage modulus, loss modulus and loss tangent as a function of oscillation frequency at 0.27% shear strain amplitude.

Further, two types of CLP-implants using DMTMM crosslinking strategy were studied which included CLP-only implants with slightly higher solid content (G1.1-CLP) and CLP-MPC implants (G2.0.x-CLP-MPC).

The DMTMM crosslinking strategy enabled further increase in the solid content in CLP-only implants. These implants with higher solid contents have superior mechanical properties for easier surgical manipulation but are also expected to degrade slowly in vivo plausibly due to surface erosion.

The storage modulus of G1.1-CLP were found to be nearly 1.5 times higher than G1.0-CLP as observed during oscillatory rheology indicating superior mechanical property. The CLP-MPC formulations (G2.0.x-CLP-MPC) were also tested for their mechanical properties and compared with CLP-only formulation. All samples were found to be stable up to around 15 Hz in a frequency sweep measurement.

The linear viscoelastic region for frequency was found to be from 0-15 Hz for all samples except CLP-MPC.

The storage moduli were found to be in the range of 14000-15000 Pa for all samples except for this sample (S4) which has a storage modulus in the range of 21000-22000 Pa. However, the viscous moduli of all samples were found to be in the similar range.

The mechanical properties of G2.0.2-CLP-MPC and G1.1-CLP were found to be very similar and the cell culture data reveal that these formulations are compatible with cell.

Figure 10:
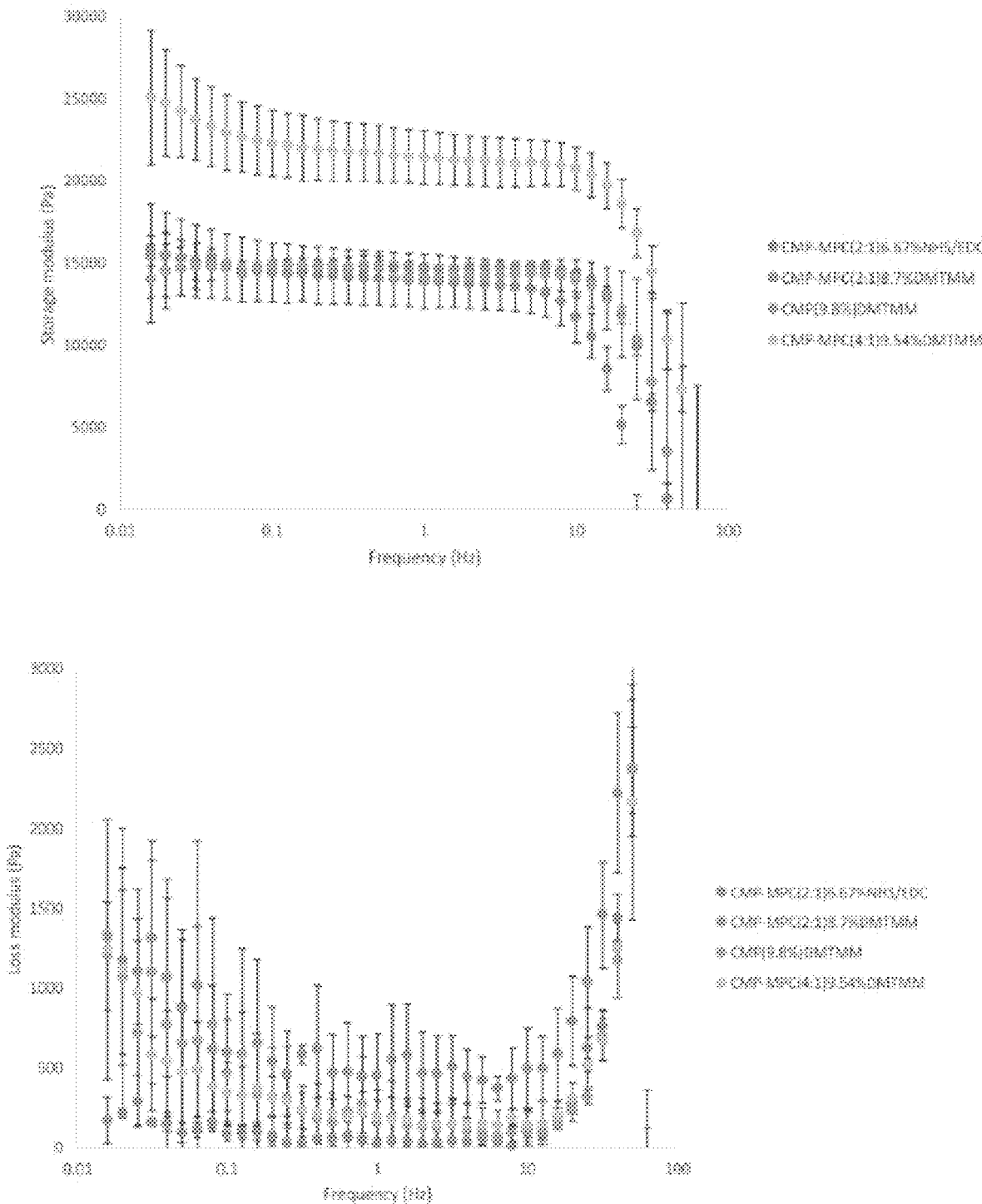
FIG. 10 depicts oscillatory rheology studies on CLP implants crosslinked with different crosslinkers.
Figure 11:
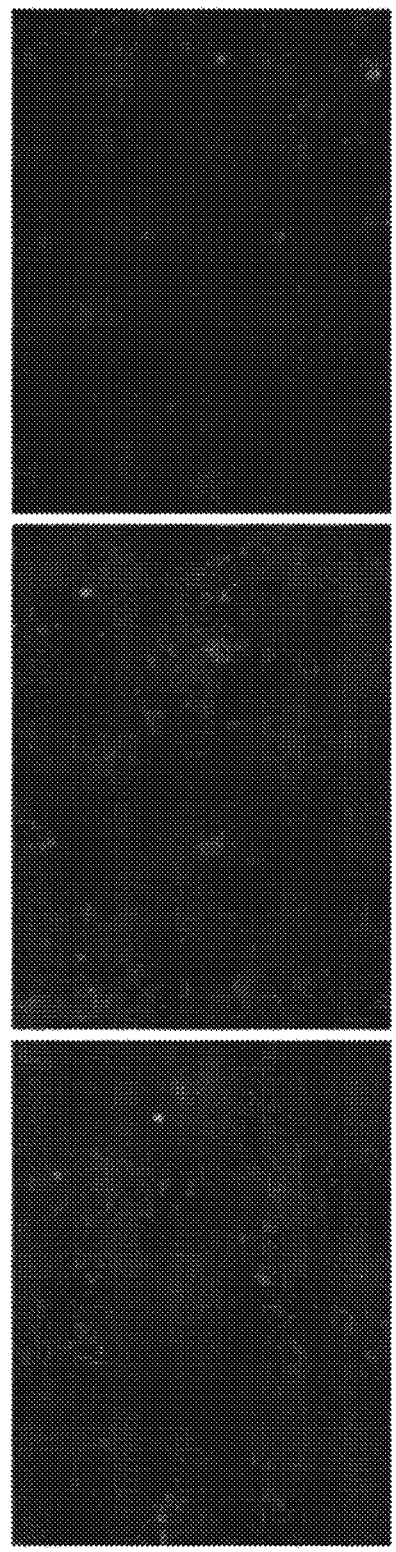
FIG. 11 depicts in vitro toxicity study wherein the growth of human corneal epithelial cells on different amounts of DMTMM on tissue culture plastic is shown.
Figure 12:
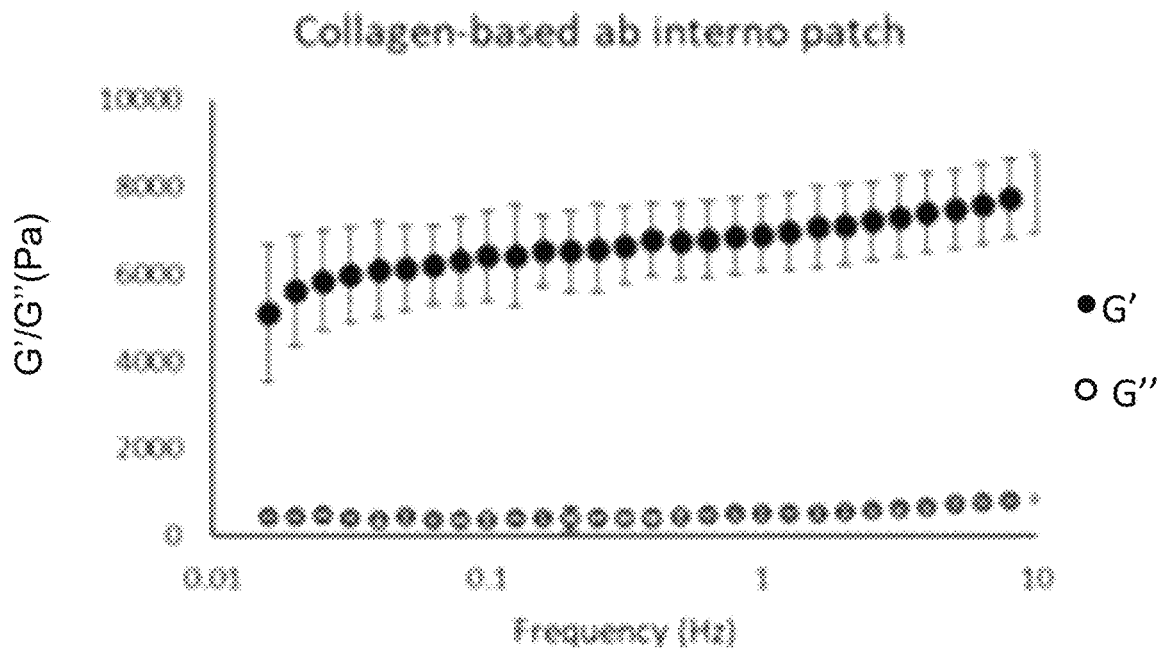
FIG. 12 shows the results of the Storage (G') and loss (G") modulus of ab interno patch (A) and CLP-PEG hydrogels fabricated as corneal implants (B) as a function of oscillation frequency at a shear strain amplitude of 0.27%. Higher G' value for the corneal implant compared to the ab interno patch indicates higher stiffness of the implant compared to the ab interno patch.
Figure 12:
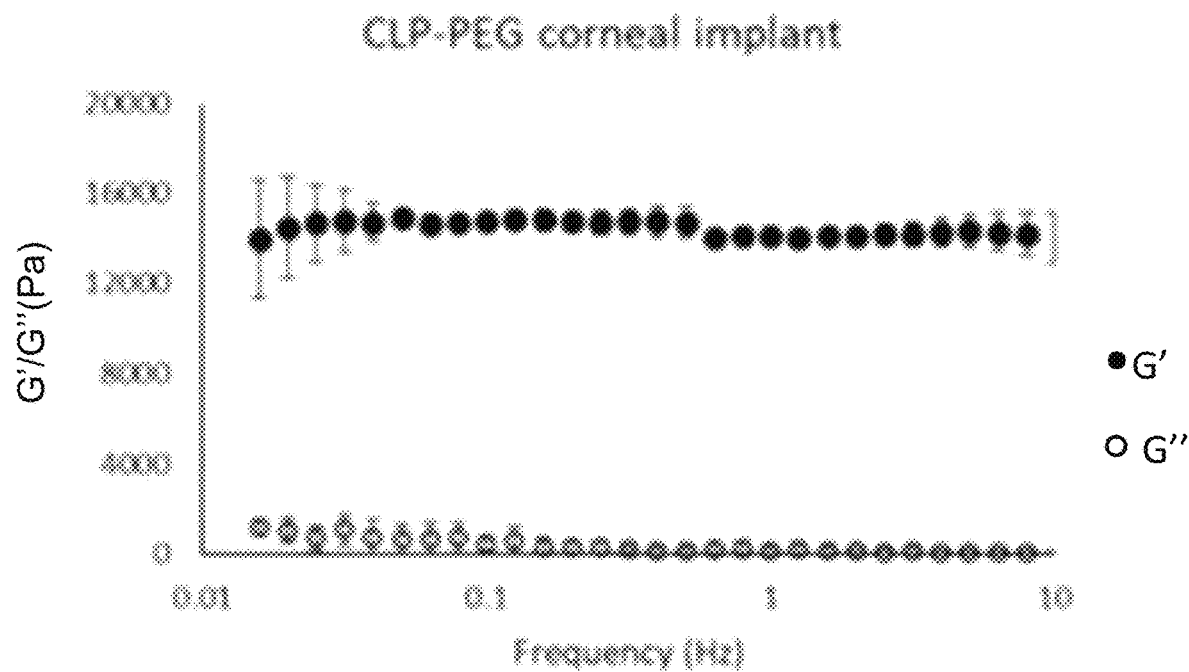

The results of the oscillatory rheology studies are depicted in FIG. 10.

Example 14: Differential Scanning Calorimetric Analysis

Differential scanning calorimetric (DSC) analysis of the hydrogels revealed glass transition temperatures ranging from 43° C. up to 63° C. depending on the equivalents of DMTMM used for crosslinking as depicted in Table 2.

TABLE 2

DSC analysis of 13% porcine collagen hydrogel crosslinked with various equivalents of DMTMM

| DMTMM equivalents | Onset temp (° C.) | $T_g$ (° C.) |
| --- | --- | --- |
| 0.4 | 43.3 ± 0.35 | 43.4 ± 0.35 |
| 0.6 | 44.9 ± 0.38 | 45.1 ± 0.18 |
| 0.8 | 39.7 ± 0.67 | 47.9 ± 0.57 |
| 1.0 | 54.5 ± 0.35 | 54.6 ± 0.41 |
| 1.5 | 62.8 | 62.9 |

The hydrogels matched the glass transition temperature of the human cornea which is 65.1° C.

Further, the calorimetric analysis of the CLP-PEG implant and operated or un-operated corneas as described in Example 9. The glass transition temperature of operated or un-operated corneas are in the range of 62-65° C. whereas the transition temperature of the initial implant was found to be 131.0±1.1° C.

TABLE 3

Thermal properties of CLP-PEG hydrogel implant and operated or un-operated corneas

| Sample | Transition Temperature (° C.) |
| --- | --- |
| CLP-PEG hydrogel | 131.0 ± 1.1 |
| Animal specimen 1 (operated cornea) | 63.1 ± 0.5 |
| Animal specimen 1 (un-operated cornea) | 63.5 ± 0.2 |
| Animal specimen 2 (operated cornea) | 62.2 ± 0.9 |
| Animal specimen 2 (un-operated cornea) | 64.3 ± 0.5 |

Figure 7:
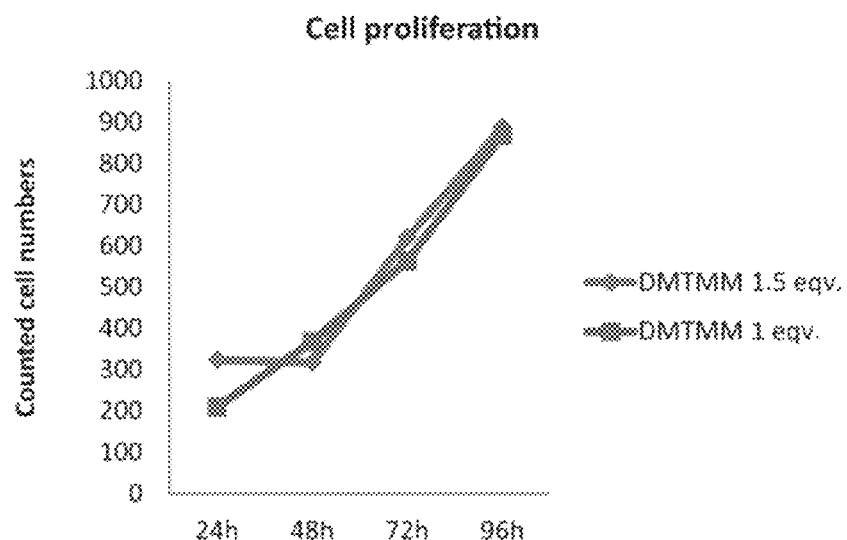
FIG. 7 shows in vitro proliferation of Human Corneal Epithelial Cells (HCEC) on implants prepared with different amounts of DMTMM.

Example 15: In Vitro Cytotoxicity Evaluation Using HCEC and Comparison with Different Crosslinkers For studying the effects of the crosslinker DMTMM on the human corneal epithelial cells, in vitro cell-culture study was performed with two formulations (DMTMM 1 eqv and DMTMM 1.5 eqv). As depicted in FIG. 7, there was no significant difference in cell-growth between these two formulations and was comparable to cell-growth on tissue culture plastic (TCP).

In another experiment, the DMTMM crosslinker was compared with EDC/NHS crosslinking system for their effects on immortalized human corneal epithelial cells.

All solutions used were sterile filtered using a 0.22 μm filter. HCEC were seeded onto 96-well tissue culture plates at a density of 10000 cells/well. They were supplemented with keratinocyte serum-free medium (KSFM; Gibco, Invitrogen, Stockholm, Sweden) containing 0.05 mg/ml bovine pituitary extract, 5 ng/ml epidermal growth factor and 1 mg/ml penicillin/streptomycin and grown to confluence in a humidified incubator at 37° C. and 5% CO2. Cells were grown to confluence prior to testing.

Figure 18:
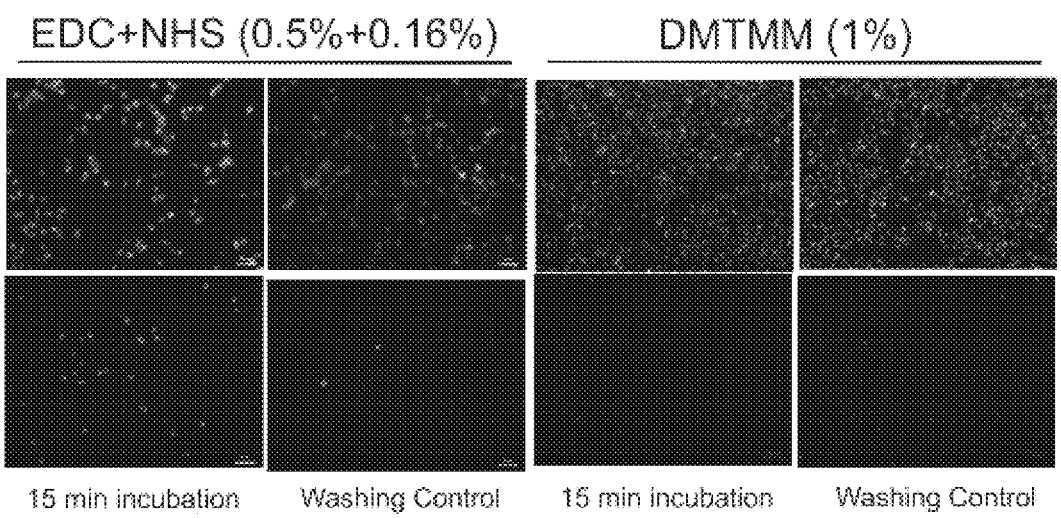
FIG. 18 shows (A) comparison of cytotoxicity of two different crosslinking system EDC-NHS and DMTMM. (B) acute toxicity of various concentrations of DMTMM.
Figure 18:
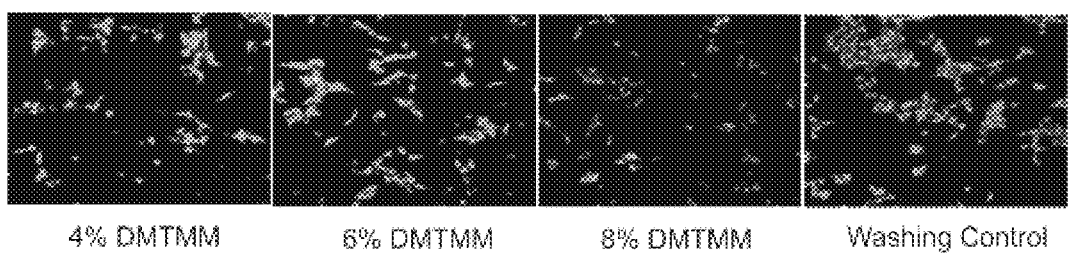
Figure 19:
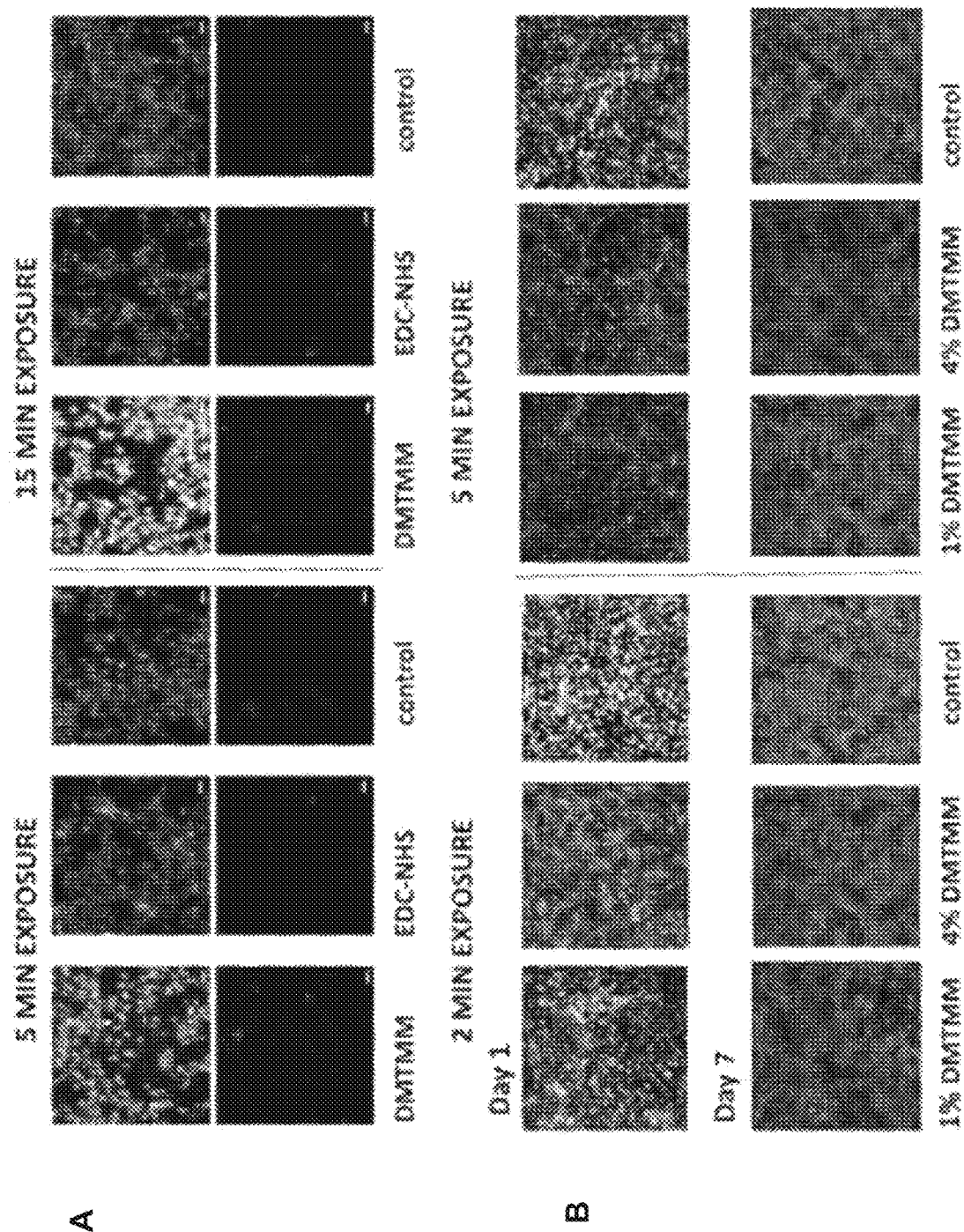
FIG. 19 shows the confluent cultured immortalised human corneal epithelial cells after exposure to protein crosslinkers in culture medium, stained with calcein-AM and ethidium homodimer-1. A) Cells after exposure to 1% (w/v) DMTMM or 0.5% EDC (w/v) with 0.16% (w/v) NHS (EDC-NHS), at day 1 after culture. Control cultures comprised culture medium only. Green cells are viable while red cells are dead. Scale bars, 50 µm. B) Cells after exposure to 1% or 4% of DMTMM for 2 min, the time needed for DMTMM to crosslink the amount of CLP-PEG needed to fill perforations and 5 min, more than double the exposure required, respectively.

One percent DMTMM (w/v) in KSFM was compared to a concentration of 0.5% (w/v) EDC and 0.16% (w/v) of its co-reactant, NHS, a crosslinker that was previously used to crosslink CLP PEG. Exposure times of 5 and 15 min were tested. The results are depicted in FIG. 18B and FIG. 19. Exposure of HCEC to 1% DMTMM or 0.5% EDC with 0.16% NHS for 5 minutes did not result in any marked differences in viability. However, more dead cells were observed in cultures exposed to EDC-NHS than DMTMM after a 15 min exposure. The live (green) and dead (red) cells immediately after incubation with EDC-NHS system revealed very high toxicity as expected even at a very low concentration (EDC+NHS—0.5%+0.16%) but very little to nearly no cytotoxicity was observed when the cells were incubated with rather high concentrations of DMTMM (1% DMTMM) for 15 min.

Example 16: Long-Term Cytotoxicity Determination of DMTMM

The results the long-term toxicity of DMTMM on HCEC was tested. HCECs were incubated for 2 and 5 min with 4% DMTMM and was kept in culture for up to 7 days. Staining for live (green) and dead (red) cells at various time points showed no toxicity caused by DMTMM. Rather the cells seemed to fully recover from any stress and grow as normally as on the tissue culture plastics (TCP) at later time points. From these experiments, it is concluded that the DMTMM crosslinking system has no long-term toxicity on cells in the required concentration range and should enable us to even encapsulate cells and eventually lead to the fabrication of corneal implants loaded with patients' own stem and stromal cells. This is unprecedented in the field of chemical protein crosslinking wherein the crosslinking system does not cause any acute or long-term toxicity on cells despite the presence of the very same functional groups in the cellular milieu.

Figure 20:
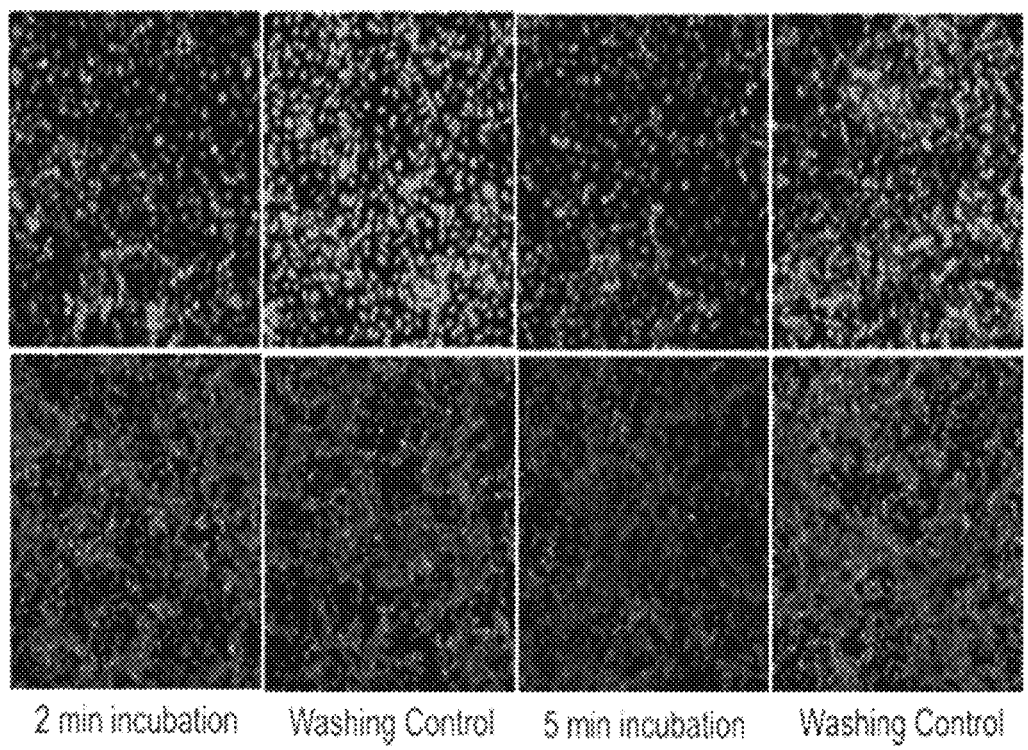
FIG. 20 shows results of studies regarding determination of long-term toxicity of DMTMM on HCECs.

FIG. 20 depicts the results of the experiments wherein the effect of 4% DMTMM has been tested on HCECs.

In another experiment to test cytotoxicity, DMTMM crosslinker at concentrations of 1 and 4% (w/v) in KSFM were then added to the cells after aspiration of culture medium. Cells were exposed to the crosslinker for 2 and 5 min, after which the crosslinker-containing medium was washed off with three rinses of KSFM.

Live-dead staining was performed using 0.01M PBS containing calcein-AM and ethidium homodimer-1 (Live/dead Viability/Cytotoxicity Kit, Invitrogen, Oregon, USA) at various time points from 1 to 7 days to evaluate the viability of HCEC. Pictures of the viable cells (green fluorescence) and the necrotic cells (red fluorescence) were taken for three different fields of view per disk using a confocal laser-scanning microscope (LSM800 Carl Zeiss, Gottingen, Germany). Control cultures consisted of cells that were exposed to culture medium only.

To determine whether cells were adversely affected over the long term, HCECs were split at 7 days after DMTMM exposure and plated onto collagen type 1-coated plates (BioCoat, Corning, USA) and the ability of the cells to stratify upon airlifting was examined at 21 days.

The results as depicted in FIG. 19B shows that increasing the concentration of DMTMM to 4% did not result in any significant changes in cell death, after an exposure of 2 min to the crosslinker. This was the amount of time required for crosslinking a 15% (w/w) aqueous CLP-PEG to form a hydrogel. After a 5 min exposure, which was more than double the exposure time required, there were more dead cells observed but most cells were still alive. Thus, DMTMM has no long term cytotoxic effects on the human corneal epithelial cells.

Example 17: Ex Vivo Perforation and Sealing

Ethical approval for the ex vivo study of bursting pressures for alternate sealing methods in standardized corneal perforations was obtained from the Moorfields Biobank Ethics Committee. Human corneoscleral buttons were mounted on an artificial anterior chamber (Barron Artificial AC; Katena, New Jersy, USA) and standardized corneal defects were made. 2 mm skin biopsy punches (Acu-Punch; Acuderm, Florida, USA) were marked at 400 µm using a 400 µm disposable astigmatic keratotomy blade as a gauge. The 2 mm punches were used to partially trephine test corneas centrally to the pre-marked depth of 400 µm. Lamellar dissection of the cap was performed with a paediatric crescent blade, leaving a residual stromal depth of approximately 400 µm. A subsequent central full thickness defect was created in the central stromal bed with a 1 mm skin biopsy punch to mimic a full thickness corneal perforation commonly encountered in clinical practice.

For testing the bursting pressure of CLP-PEG/Fibrinogen glue and fibrin glue, standardized corneal defects were made on porcine corneoscleral buttons. A 4 mm punch was used to partially trephine test corneas centrally to a depth of approx. 200 µm. Lamellar dissection of the cap was performed with a pediatric crescent blade, leaving a residual stromal depth which was then trephined with a 3 mm punch to a depth of approx. 200 µm. A subsequent central full thickness defect was created in the central stromal bed with a 1mm skin biopsy punch to mimic a full thickness corneal perforation commonly encountered in clinical practice.

After preparation of standardized corneal perforations as described above, the experimental conditions for sealing the corneal defect were tested. Five types of sealing methods were tried.

The first sealing method was the current standard treatment ab externo patching using cyanoacrylate glue and a 3 mm clear plastic patch. In brief, an air bubble was inserted via a paracentesis to help create a dry ocular surface, and arrow-tip surgical sponges were used to dry any residual fluid after corneal epithelial debridement around the standard perforations. 3 mm plastic patches were punched from a clear polyethylene surgical drape (Unomedical Sterile Surgical Drapes, Oklahoma City, USA) using a skin-biopsy punch. A single patch was applied externally directly onto the test defects after coating with cyanoacrylate glue. Using the same method, the corneal defects were sealed using fibrin glue.

The second sealing method was using the 100 µm thickness chemically crosslinked collagen-hydrogel ab interno patch alone. A collagen hydrogel sheet that could be cut into the required shape, inserted and positioned with an air bubble as in DSAEK surgery was evaluated.22 Here, a 3.2 mm 3-step limbal incision was made with a surgical keratome through which a 3 mm diameter disc of the test hydrogel was inserted with forceps. Discs were positioned under the defect and floated into place using an air bubble, as in endothelial keratoplasty. Patches were centred with a 30-gauge needle. Once a satisfactory position was achieved, the infusion was increased and bursting pressures were measured.

The third condition was the collagen-hydrogel ab interno patch coupled with the CLP-PEG filler glue. Hydrogel based ab interno patches were inserted as given in the second sealing method. A single drop of fibrin glue was placed into the defect to coat the base and walls of the defect. Subsequently, the CLP-PEG filler glue was administered to completely fill the defect and the anterior surface was smoothed with a cellulose ophthalmic sponge (Weck-Cel; Beaver-Visitec, Massachusetts, USA) to resemble the anterior corneal surface. After drying, the infusion was increased and bursting pressures were measured.

The fourth condition was using CLP-PEG-Fibrinogen glue in combination with thrombin. The defect was coated with 250 U/mL thrombin. The CLP-PEG-Fibrinogen glue was injected to completely fill the defect. After allowing the CLP-PEG-Fibrinogen glue to dry the infusion was increased and the bursting pressures were measured.

Figure 13:
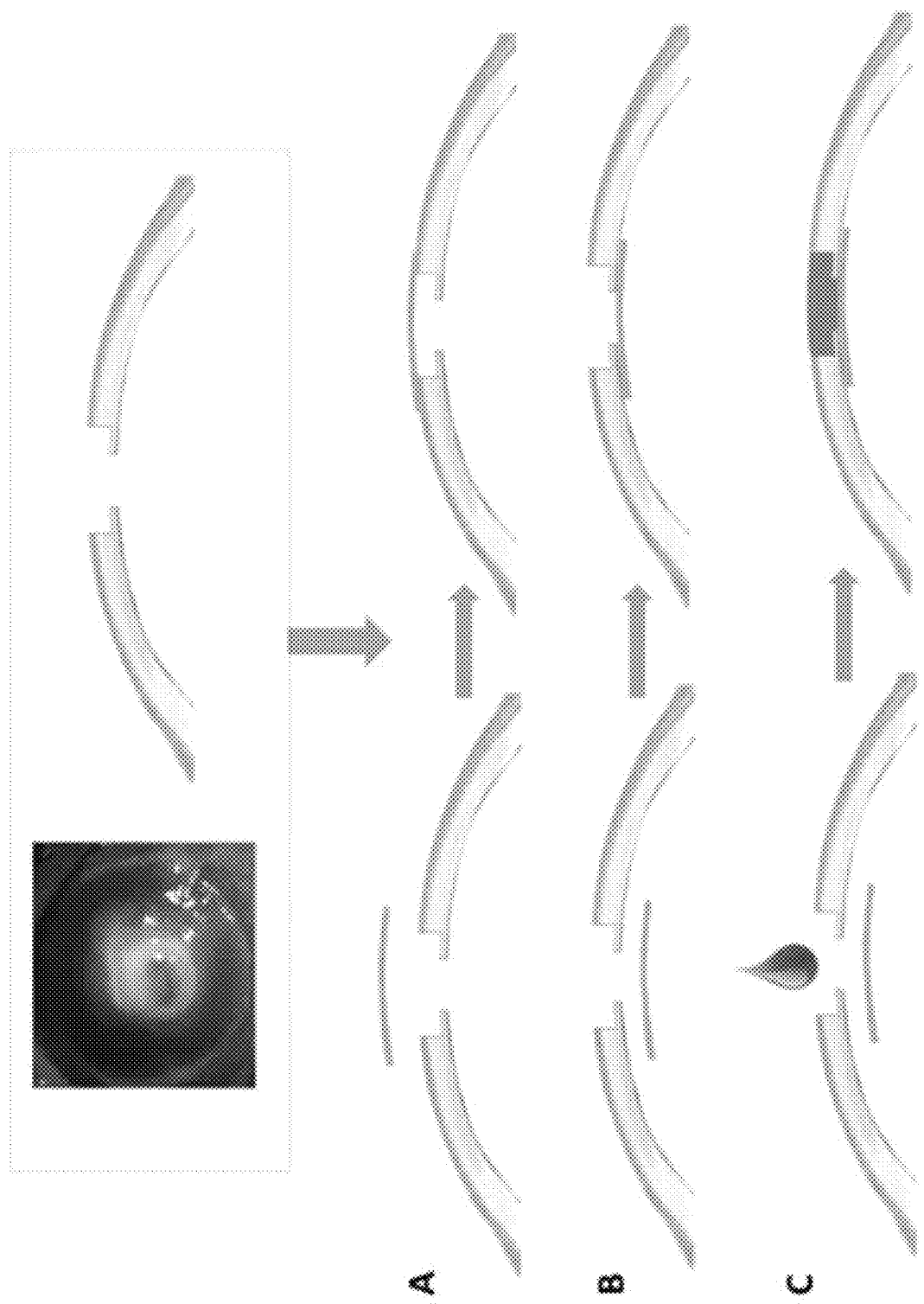
FIG. 13 depicts the three modes of patching which were tested: A) A cyanoacrylate glue patch applied externally to the standardized defect. The glue was applied to the internal surface of a 3 mm plastic disc cut from a surgical drape and applied to the cornea. B) A 100.mu.m, 3 mm diameter crosslinked collagen patch was applied internally to the standardized defect as an ab interno patch. C) Combination of a 100.mu.m, 3 mm collagen ab interno patch with external application of the CLP-PEG filler glue to seal the standardized defect and replace lost corneal tissue.

FIG. 13 shows an example of a human cornea with a macro-perforation and a diagrammatic scheme showing recreation of such a defect in a simplified, standardized ex vivo human corneal model. The standardized defect comprised a central full thickness defect of 1 mm in diameter with a surrounding partial thickness defect of 2 mm in diameter and a depth of 400 µm. The three modes of patching tested were as follows: A) A cyanoacrylate glue patch applied externally to the standardized defect. The glue was applied to the internal surface of a 3 mm plastic disc cut from a surgical drape and applied to the cornea. B) A 100 µm, 3 mm diameter crosslinked collagen patch was applied internally to the standardized defect as an ab interno patch. C) Combination of a 100 µm, 3 mm collagen ab interno patch with external application of the CLP-PEG hydrogel to seal the standardized defect and replace lost corneal tissue.

Example 18: Bursting Pressure Evaluation

For evaluating the bursting pressure of the seals made in the previous example, Artificial anterior chambers were connected via an intra-arterial blood pressure monitor (Infinity 540; Draeger, Lubeck, Germany) to a normal saline infusion using a blood pressure cuff to regulate infusion pressure. After application of test patches, the infusion pressure was increased until the seal gave way, resulting in fluid egress. Bursting pressure (mmHg) was then recorded as the peak in a continuous trace of infusion pressure verses time. A one-way ANOVA followed by a Tukey post-hoc test was used to compare the difference in bursting pressures among the three conditions. The bursting pressures recorded for the three different patching modalities is summarized in Table 4.

TABLE 4

Bursting pressures (mmHg) for various materials tested. Though cyanoacrylate glue had the highest bursting pressures (p < 0.0001), there was a 30% failure rate (where no seal was achieved) that was not seen with the other materials.

| Case | Cyanoacrylate Glue | Fibrin glue | 100 μm patch* | 100 μm patch plus CLP-PEG filler-glue§ | CLP-PEG-Fibrinogen glue |
|---|---|---|---|---|---|
| 1 | 334 | 243 | 47 | 79 | 168 |
| 2 | 10 | 278 | 49 | 91 | 185 |
| 3 | 350 | 255 | 42 | 85 | 147 |
| 4 | 247 | 260 | 55 | 84 | 180 |
| 5 | 5 | | 41 | 94 | |
| 6 | 331 | | 44 | 92 | |
| 7 | 312 | | 48 | 91 | |
| 8 | 326 | | 52 | 79 | |
| 9 | 339 | | 41 | 83 | |
| 10 | 11 | | 44 | 88 | |
| 11 | 350 | | | | |
| 12 | 347 | | | | |
| 13 | 323 | | | | |
| Mean | 325.9 | 259 | 46.3 | 86.6 | 170 |
| SD | 30.4 | 14.5 | 3.7 | 5.4 | 16.9 |

*100 μm collagen hydrogel ab interno patch
§100 μm hydrogel ab interno patch plus externally applied CLP-PEG glue
cases where a seal was not achieved. These results were not included in the calculation of mean or standard deviation
SD = standard deviation Conventional ab externo patching using cyanoacrylate glue achieved the highest bursting pressure with a mean (standard deviation) bursting pressure of 325.9±30.4 mmHg followed by ab externo patching using fibrin glue. However, the surface obtained was rough and in 3 of 13 experimental perforations, leaking occurred in using cyanoacrylate glue as seals failed to form.

Ab interno patching using 100 μm thick collagen hydrogels produced an effective seal in 10 out of 10 samples. However, while an adequate seal was achieved, the mean bursting pressure was only 46.3±3.7 mmHg and bulging of the patch was observed.

Bulging was less evident with the use of the CLP-PEG filler-glue in conjunction with the 100 μm ab interno patch, as the CLP-PEG filler-glue reinforced the hydrogel patch, helping to prevent its protrusion through the corneal defect. A higher mean bursting pressure was observed with this technique (86.6±5.4 mmHg).

Though best results were obtained using the cyanoacrylate glue, it lacks the effectiveness CLP based hydrogels. Amongst, hydrogels based on CLP-PEG, CLP-PEG-Fibrinogen glue gave the best results as compared to the other CLP-PEG based hydrogels.

Figure 14:
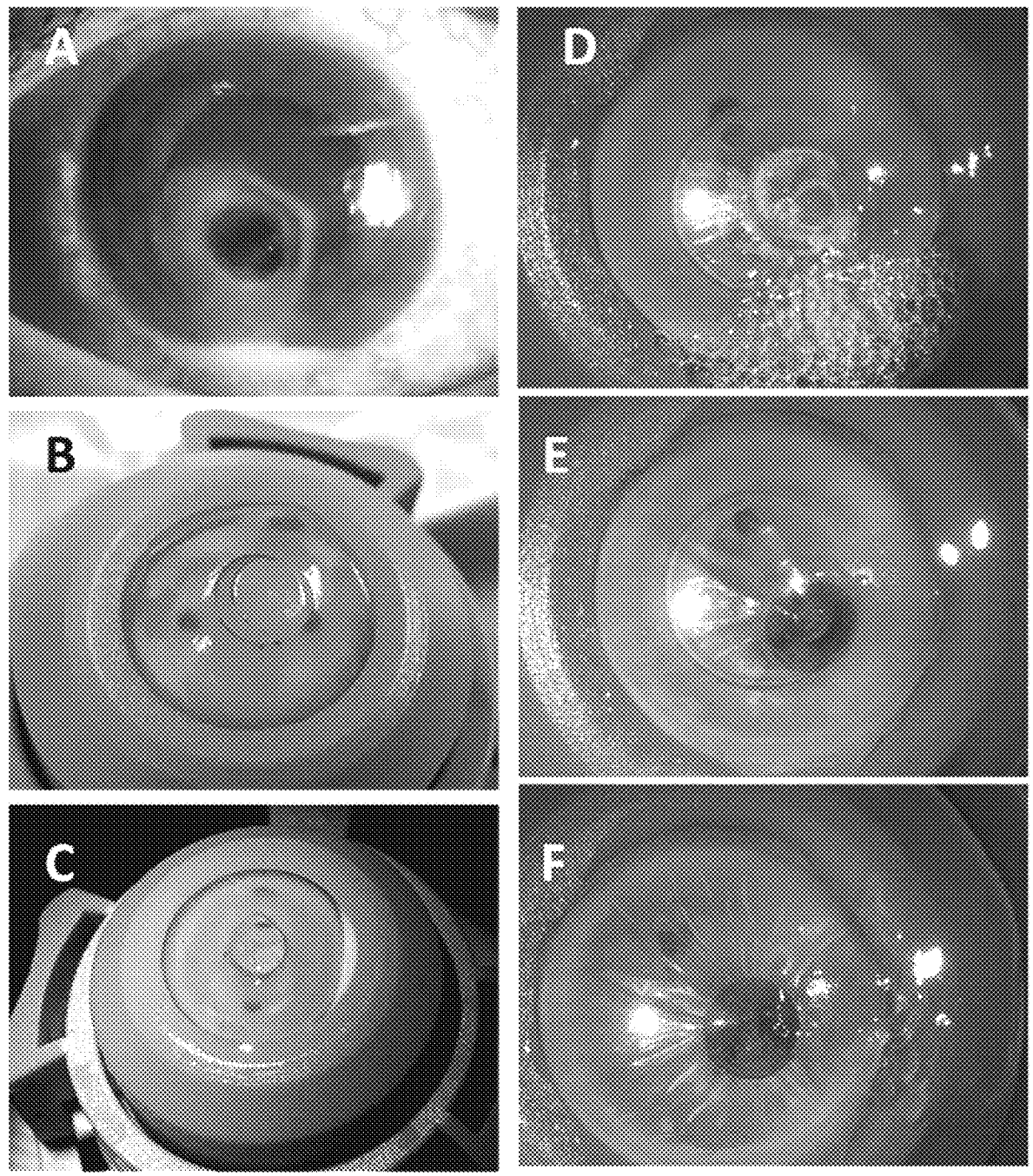
FIG. 14 depicts A) example of a perforated human cornea. B) experimental set up showing an in vitro perforated corneal model within an artificial anterior chamber device. C) perforated cornea model filled with CLP-PEG containing fibrin glue. Other vitro cornea models patched with D) conventional ab externo patching with cyanoacrylate glue (control), E) a collagen hydrogel as an ab interno patch only, F) collagen hydrogel an interno patch with CLP-PEG filler.

FIG. 14 depicts A) example of a perforated human cornea. B) experimental set up showing an in vitro perforated corneal model within an artificial anterior chamber device. C) perforated cornea model filled with CLP-PEG containing fibrin glue. Other vitro cornea models patched with D) conventional ab externo patching with cyanoacrylate glue (control), E) a collagen hydrogel as an ab interno patch only, F) collagen hydrogel an interno patch with CLP-PEG filler.

Example 19: Suturability of the Corneal Implants

Figure 8:
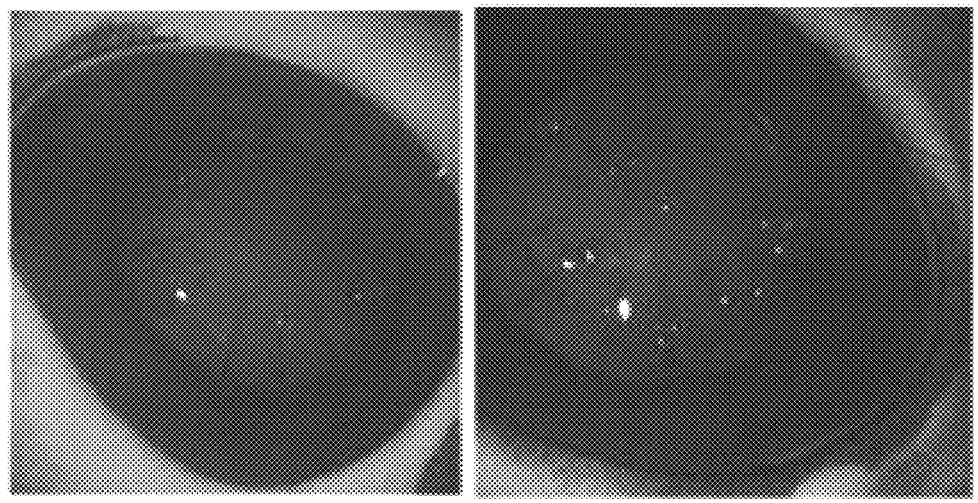
FIG. 8 shows in vitro suture test on excised pig eyes.

The suturability of the hydrogels was tested on excused pig eyes by placing 12 interrupted sutures and the implants were found to withstand multiple interrupted sutures with little breaks. The results of in vitro sutures test on excised pig eyes are depicted in FIG. 8.

Figure 15:
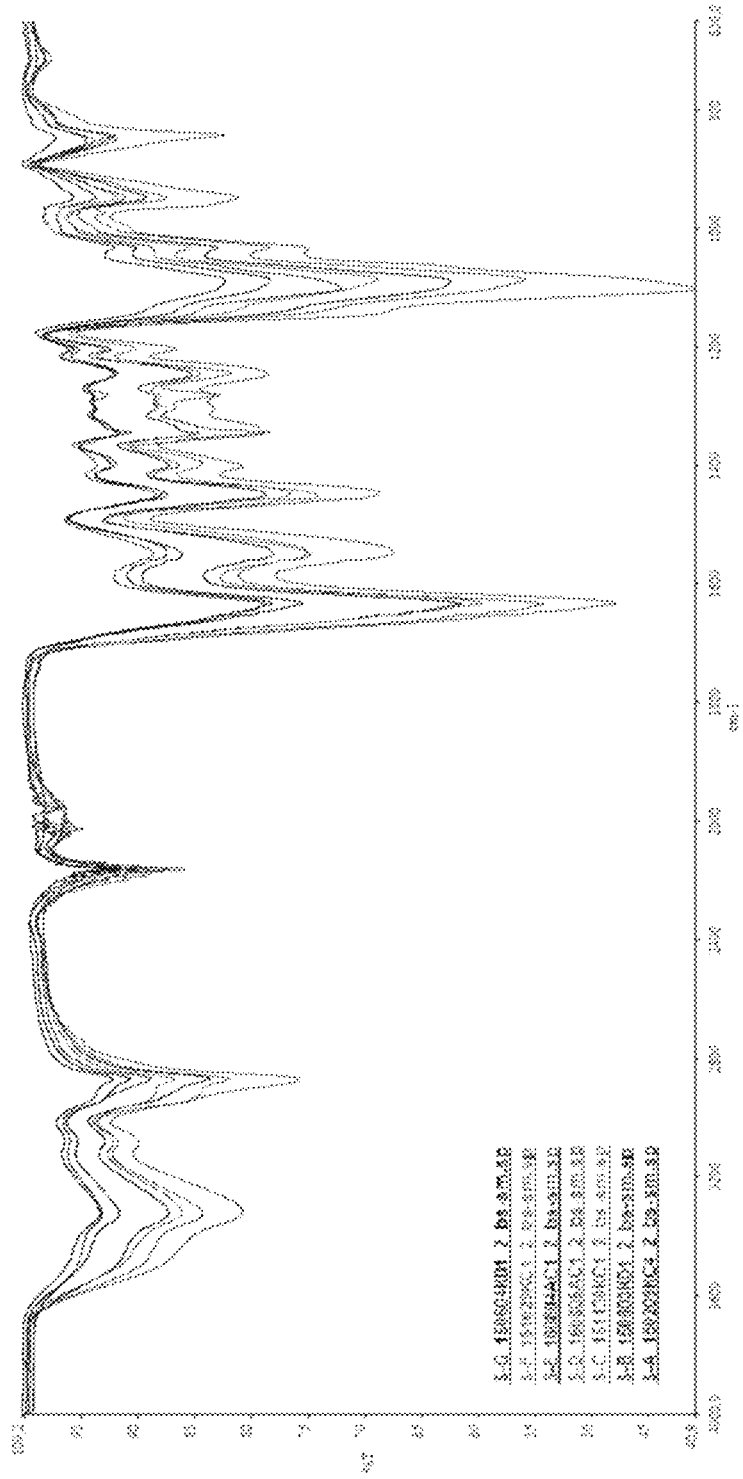
FIG. 15 depicts the results of FTIR studies showing overlay of IR spectrum of 7 different implant samples stored for various durations ranging from 14 months to 10 days

Example 20: FTIR Spectroscopy of Hydrogel to Evaluate Long-Term Integrity of Sample The storage conditions of the developed CLP implants were tested. CLP-PEG hydrogels either freshly made or stored over a long period were subjected to FTIR spectroscopy to check for any changes in the spectra. For this purpose, hydrogels were frozen with liquid nitrogen and lyophilised. The lyophilised dry hydrogels were subjected to FTIR spectroscopy on a Perkin Elmer IR spectrophotometer using universal ATR. Samples were subjected to a wave-scan ranging 650-4000 $cm^{-1}$. The results are summarised in FIG. 15. No significant differences in the spectra could be found between samples indicating the integrity of the implants over the storage duration of 10 days to 14 months.

Example 21: Corneal Thickness Measurement

The hydrogels prepared in the previous examples were grafted into New Zealand white male rabbits by deep anterior lamellar keratoplasty (DALK) to determine their capability for corneal regeneration. Implants were strong enough to tolerate trephination, implantation procedure and suturing. No adverse inflammatory reactions were observed in 3 of 4 rabbits post-operatively. At 1 month post-operatively all implants and surrounding rabbit corneas were clear with full epithelial coverage, as demonstrated by fluorescein staining. Healing process was accompanied by mild cornea neovascularization in all animals. However, neovessels gradually resolved and were absent at 3 months after implantation in all animals. However, all implants remained transparent and covered with epithelium.

Corneal thickness changes of both eyes of all animals before and in different time points after surgery is presented in Table 5. Intraocular pressure remained within normal ranges in all animals.

TABLE 5

Central corneal thickness (μm, M ± SD) of both eyes of all animals before and in different time points after surgery.

| | | Time point | | |
|---|---|---|---|---|
| Rabbit # | Eye | Before | 1 month | 3-month |
| 2575 | OD (Oculus dexter) | 390 ± 3.9 | 321 ± 5.4 | 293 ± 1.2 |
| | OS (Oculus sinister) | 392 ± 6.5 | 428 ± 2.3 | 399 ± 7.8 |
| 2645 | OD (Oculus dexter) | 388 ± 4.2 | 464 ± 5.2 | 382 ± 3.5 |
| | OS (Oculus sinister) | 378 ± 2.5 | 361 ± 3.2 | 399 ± 7.6 |
| 2653 | OD (Oculus dexter) | 383 ± 1.0 | 289 ± 3.6 | 313 ± 2.9 |
| | OS (Oculus sinister) | 364 ± 3.3 | 395 ± 8.0 | 385 ± 4.6 |
| 2654 | OD (Oculus dexter) | 340 ± 2.8 | 318 ± 8.6 | 363 ± 9.9 |
| | OS (Oculus sinister) | 342 ± 9.3 | 360 ± 3.8 | 335 ± 2.4 |

Example 22: In Vivo Safety Evaluation in Pigs

In compliance with the OECD Principle of Good Laboratory Practice (GLP), NV/MC/CHEM (98) 17, 1997, and with local ethical permission from Stockholms Norra Djurförsöksetiska Nämnd, CLP-PEG implants comprising 9.7% CLP (w/w) crosslinked with DMTMM were grafted into the corneas of four Gottingen mini-pigs that had received controlled alkali burns. Implants comprising CLP-PEG with incorporated MPC, comprising 8.5% CLP, were tested in the animals.

Implants 6.75 mm in diameter and 500 µm thick were implanted into one cornea of each pig by anterior lamellar keratoplasty after excision of a 500 µm thick, 6.5 mm button of the pig's own central corneal tissue under full anaesthesia. The implants were held in place with overlying sutures. An antibacterial and anti-inflammatory ophthalmic solution (TOBRASONE®, suspension with 3 mg/mL dexamethasone and 1 mg/mL tobramycine, Alcon, Sweden) was administered post operatively for 5 weeks, at which point the sutures were removed. The corneas were monitored for any adverse effects for a period of 12 months.

FIG. 16 shows all 8 operated animals at 12 months post-operation. Some blood vessels are seen in the eyes along with haze. Overall, the haze and vascular is slightly more prominent and even within the CLP-PEG group while the haziness in the MPC containing group is peripheral within the implant. Analyses of the collagen content showed that CLP-PEG implants had a higher overall content of collagens 1 and V than healthy unoperated corneas, while CLP-PEG-MPC implants had overall significantly less collagen. However, CLP-MPC showed a similar amount of high molecular weight, i.e. mature collagen fibrils as the healthy unoperated controls.

Example 23: Anti-Scarring Properties of the Hydrogel

For analyzing the anti-scarring properties of the hydrogels, CLP only and CLP containing a RGDSPG motif as represented by SEQ ID NO:8 from fibronectin were tested.

Figure 21:
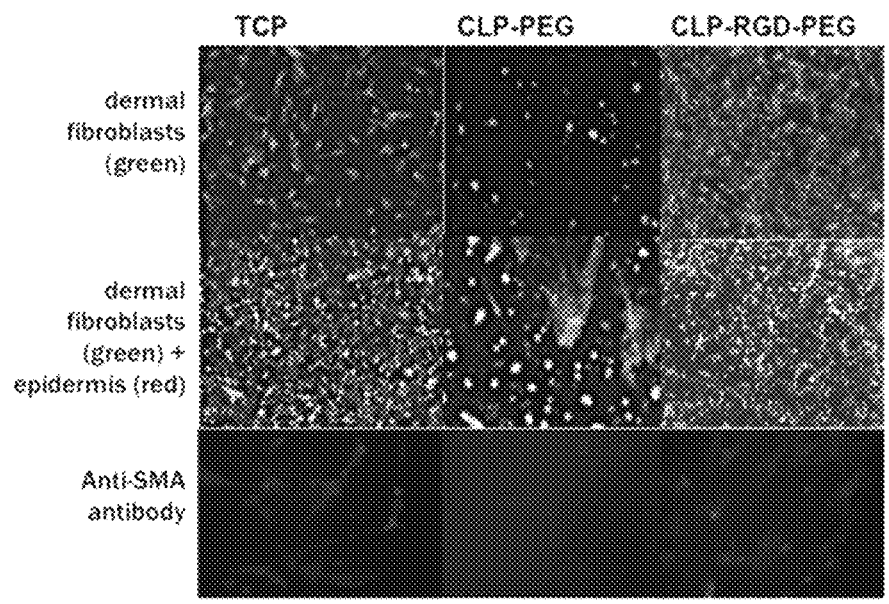
FIG. 21 shows skin dermal fibroblasts and epidermal keratinocytes on CLP-PEG hydrogels with and without RGD. Control cells are grown on tissue culture plastic (TCP). Fibroblasts are supported by TCP and CLP-RGD-PEG. These are positively stained with an anti-body against smooth muscle actin (SMA) suggesting that these cells are activated fibroblasts.

Skin dermal fibroblasts and epidermal keratinocytes on CLP-PEG hydrogels with and without RGDSPG were tested. Control cells were grown on tissue culture plastic (TCP). Fibroblasts were supported by TCP and CLP-RGD-SPG-PEG. These are positively stained with an anti-body against smooth muscle actin (SMA) suggesting that these cells are activated fibroblasts. FIG. 21 depicts the results of the experiment.

In another experiment, the comparative properties of dermal fibroblasts cultured on tissue culture plastic (TCP), porcine type I collagen hydrogels (PC) and CLP-PEG and CLP-RGDSPG-PEG hydrogels were studied.

The fibroblasts were activated by plating on TCP without any treatment. Some fibroblasts were treated using TGF-beta (10 ng/mL) prior to seeding onto the substrates ("pre-treated") or after seeding onto the substrates ("post-treated"). Similarly, porcine type I collagen hydrogels (PC), CLP-PEG and CLP-RGDSPG-PEG hydrogels were also treated and activated as shown by the positive staining by anti-SMA antibody.

Figure 22:
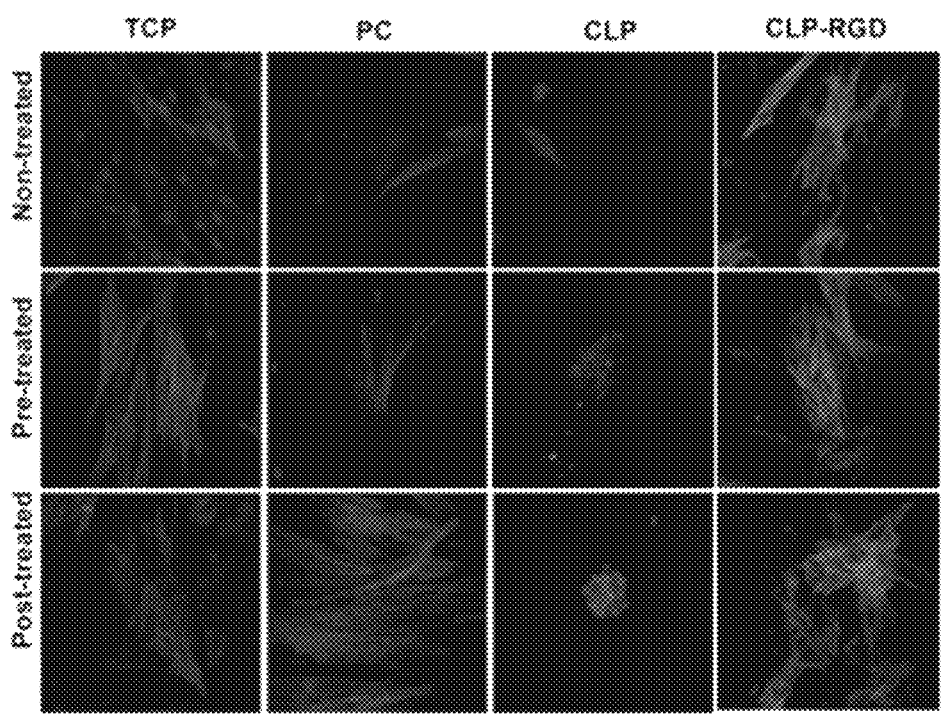
FIG. 22 depicts results of in vitro culture of primary dermal fibroblasts on tissue culture plastic (TCP) and hydrogels of porcine collagen (PC), CLP-PEG (CLP) and CLP-RGD-PEG (CLP-RGD). The cells were left untreated or treated with TGF-beta (10 ng/ml) prior to seeding onto the substrates ("pre-treated") or after seeding onto the substrates ("post-treated"). Red staining indicates cells that are positive for smooth muscle actin. DAPI counterstain of nuclei appear blue.

FIG. 22 exhibits the in vitro culture of primary dermal fibroblasts on tissue culture plastic (TCP) and hydrogels of porcine collagen (PC), CLP-PEG (CLP) and CLP-RGD-SPG-PEG (CLP-RGD). The cells were left untreated or treated with TGF-beta (10 ng/ml) prior to seeding onto the substrates ("pre-treated") or after seeding onto the substrates ("post-treated"). Red staining indicates cells that are positive for smooth muscle actin. DAPI counterstain of nuclei appear blue. The results show the ability of CLP analogs to be potentially used as regeneration scaffolds or templates, pre-formed or in situ cured, to have an anti-scarring effect.

Example 24: Induction of Extracellular Vesicle Production

Mini-pig neo corneas were investigated to characterize the exosomes and immunohistochemistry performed on sections of implanted with CLP-PEG and RHCIII-MPC showed differential staining for CD9 marker for exosomes, and Rab-7, a marker for endosomes.

TEM images of the mini-pigs implanted with RHCIII-MPC and CLP-PEG implants show a characteristic basal surface morphology with numerous invaginations and exosome like vesicles below the basal surface.

CLP-PEG implanted corneas showed increased staining for CD9 but not the RHCIII-MPC compared to healthy unoperated controls.

Both CLP-PEG and RHCII-MPC implanted corneas showed an increase in staining for Rab7. Further examination was done in in vitro studies by culturing human corneal epithelial cells on the CLP-PEG and RHCIII-MPC implants. A network of CD9 stained vesicles connecting the cells both in CLP-PEG and RHCIII-MPC implants was observed.

On the other hand, Rab7 stained vesicles exclusively remained intracellular and were increased in cells cultures in both the implants compared to tissue culture plastic.

Therefore, it is concluded that cell-free CLP-PEG implants in the cornea promotes regeneration. There was an elevated release of exosomes in these implants compared to RHCIII-MPC implants. Examination of their cargo showed these included collagen and other macromolecules associated with repair and regeneration. CLP-PEG implants are able to stimulate exosome production in vitro, in cell cultures when seeded with corneal epithelial cells. Therefore, CLP-PEG stimulates production of the exosomes that in turn promoted regeneration.

Figure 23:
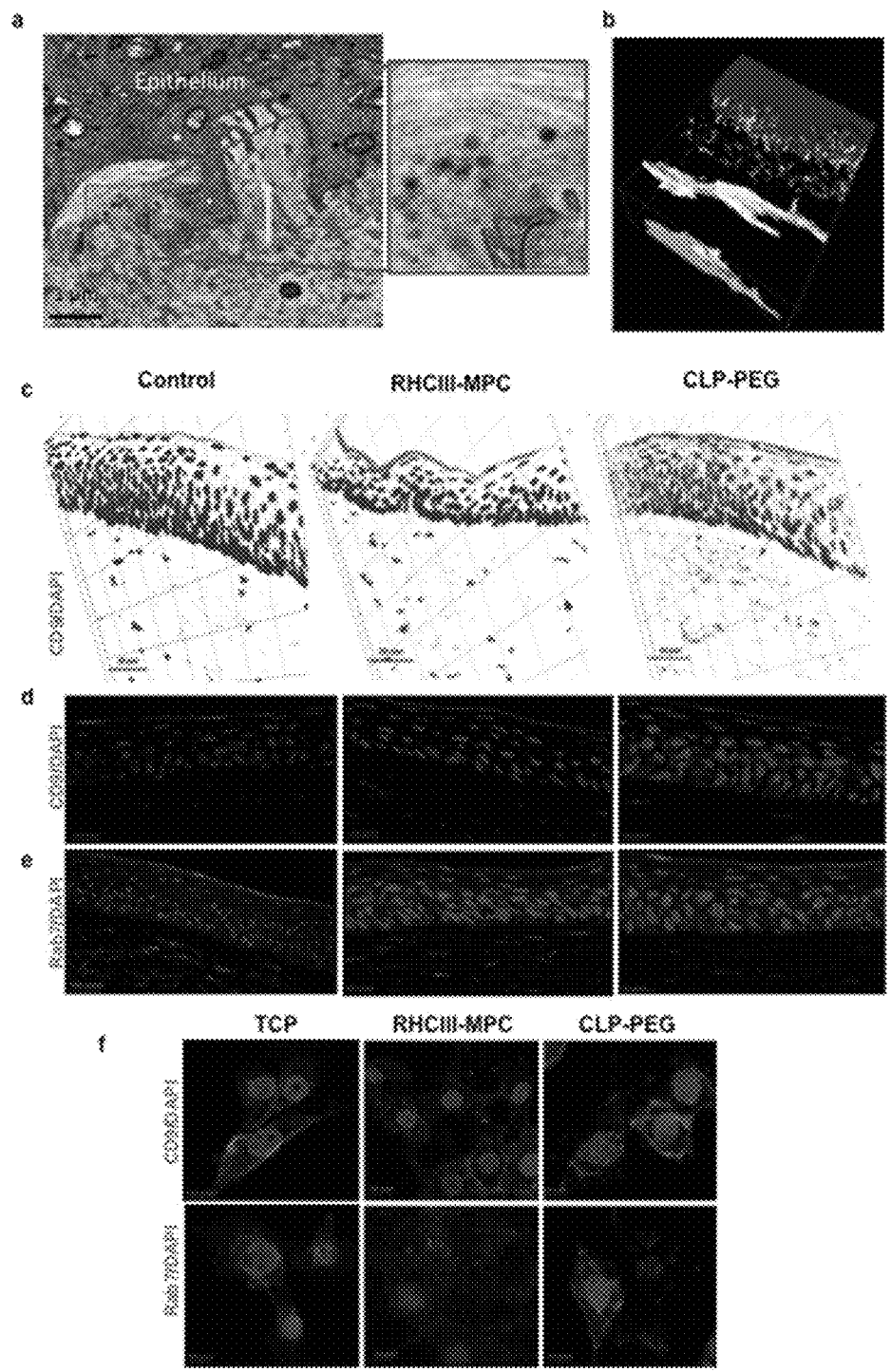
FIG. 23 depicts (a) shows TEM of cornea of a mini-pig implanted with CLP-PEG at 12 months post-operation. The regenerated neo-cornea epithelial-stromal interface region shows production of electron dense extracellular vesicles. These were visualized by 3D reconstruction of en bloc face SEM sections. (b) shows the extracellular vesicles as yellow colored (c) is a 3D reconstruction of CD9-positive extracellular vesicles of control, RHC-III MPC and the CLP-PEG. (d) immunohistochemically labelled sections of CD9-positive extracellular vesicles (e) shows EVs stained for Rab7 (f) shows differential EV patterns in corneal epithelial cells cultured on the different substrates.

FIG. 23 depicts the results of the experiments.

FIG. 23 (a) shows TEM of cornea of a mini-pig implanted with CLP-PEG at 12 months post-operation. The regenerated neo-cornea epithelial-stromal interface region shows production of electron dense extracellular vesicles. These were visualized by 3D reconstruction of en bloc face SEM sections. FIG. 23 (b) shows the extracellular vesicles as yellow colored. FIG. 23 (c) is a 3D reconstruction of CD9-positive extracellular vesicles of control, RHC-III MPC and the CLP-PEG. The immunohistochemically labelled sections are labelled sections in FIG. 23 (d). FIG. 23 (e) shows EVs stained for Rab7. FIG. 23(f) shows differential EV patterns in corneal epithelial cells cultured on the different substrates.

Example 25: Enhancement of Cellular Specificity and Growth

Implants prepared by CLP-PEG incorporated with RGD-SPG and IKVAV peptide motifs as represented by SEQ ID NO: 12 and SEQ ID NO:14 were used.

Morphology, as well as proportions of the various cell types, was dependent upon the presence of cell adhesion peptide sequences as well as percentage solid content of the CLP-PEG hydrogels. Cerebellar explants on the surface of 6% (w/w) CLP-PEG hydrogels differentiated into confluent layers of microglia with neuronal-astrocyte rings on top resembling the glial tubes of retina and optic nerve as depicted in the results. On 12% (w/w) CLP-PEG hydrogels, cells growing out from the cerebellar explants did not adhere as tightly to the hydrogel surfaces and instead formed small spheroids after plating.

The ensuing outgrowth of astrocytes and neurons retained the spheroidal structures. Incorporating of RGDSPG and IKVAV sequences within 12% (w/w) hydrogels increased cellular adhesion and stimulated the outgrowth of longer neurites in comparison to CLP alone, resulting in a larger area covered per neuron, particularly in CLP-RGDSPG containing hydrogels.

CLP-RGDSPG-PEG produced an evenly distributed neuronal-glial culture with high neurite density and amoeboid-shaped microglia that were physically entangled within the neuron-astrocyte mat. On CLP-IKVAV-PEG, however, the neuronal-astrocyte network that differentiated was organized into discrete bundles of neurons and microglia had either round or rod-shaped morphologies.

Similar to the differential growth of neural cells on CLP tagged with of cell attaching peptides compared to the CLP alone, primary skin fibroblasts show hampered growth on the CLP alone gels while show enhanced cell attachment and proliferation in the presence of RGDS. These results showcase the pivotal role of cell attaching peptides to optimize the cell binding, proliferation and differentiation capabilities of the implants that mimics the original collagen protein. Use of CLP-PEG crosslinked with DMTMM as solid implants or as fillers that incorporate these other bioactive motifs will allow for regeneration of cornea (or skin) wounds without transplantation.

Figure 24:
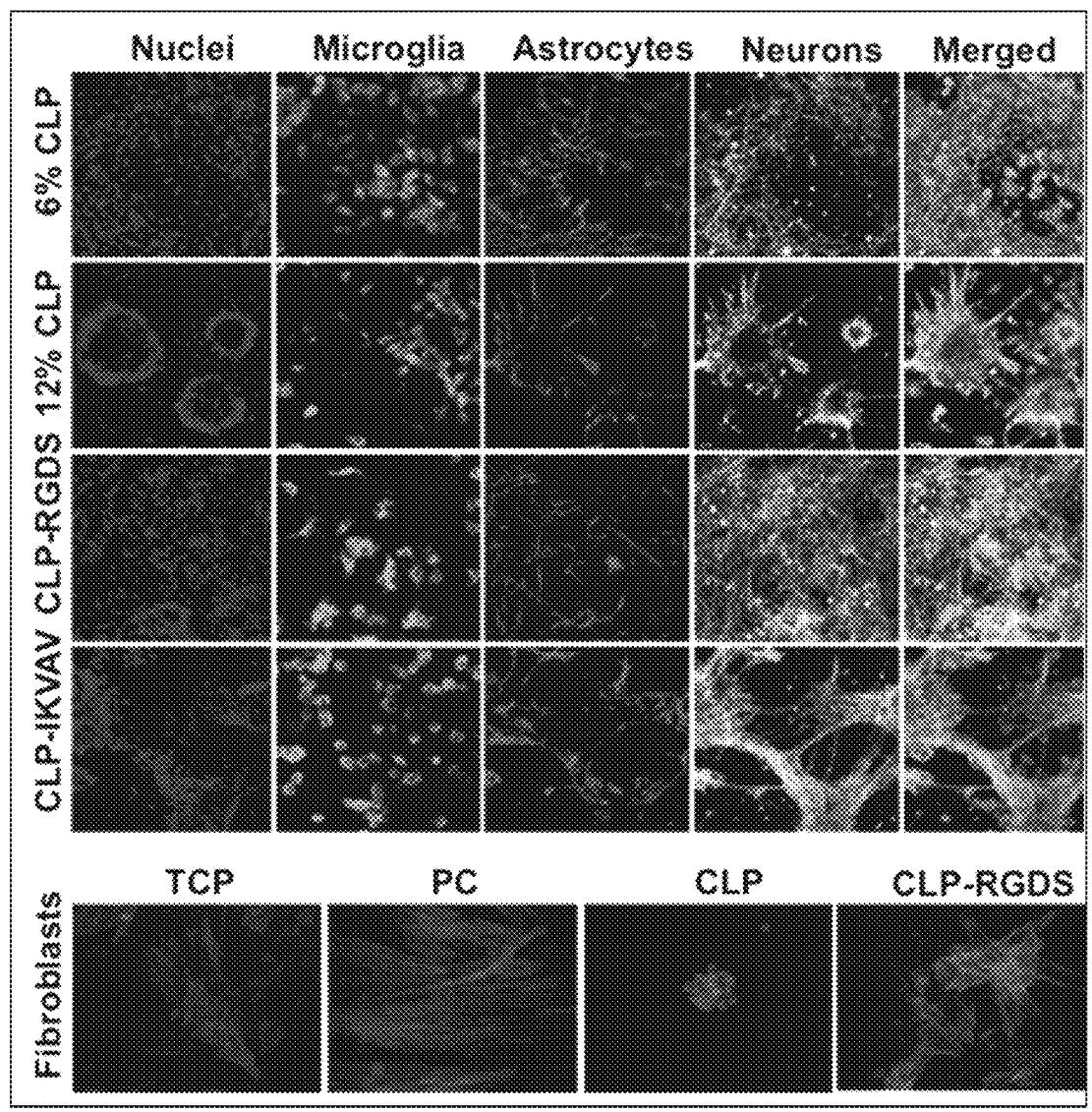
FIG. 24 shows primary neurons and glia from rat cerebellum on day 6 in vitro after planting on 6% and 12% CLP-PEG that have incorporated RGDSPG and IKVAV peptides. Neurons (yellow) are immunolabelled with anti-microtubule-associated protein 2, and astrocytes (red) with anti-glial fibrillary acidic protein. Microglia are stained green with isolectin GS-IB4. All nuclei are stained blue with Hoechst33342.

FIG. 24 shows primary neurons and glia from rat cerebellum on day 6 in vitro after planting on 6% and 12% CLP-PEG, and CLP-PEG that have incorporated RGDS and IKVAV peptides. Neurons (yellow) are immunolabelled with anti-microtubule-associated protein 2, and astrocytes (red) with anti-glial fibrillary acidic protein. Microglia are stained green with isolectin GS-IB4. All nuclei were stained blue with Hoechst33342. Also shown are fibroblasts which are activated by the presence of RGDS but CLP alone will not support these scar regenerating cells, even though they clearly support nerves and glia.

We claim:

1. A hydrogel comprising CLP-PEG, wherein the collagen-like peptide (CLP-PEG) comprises a conjugate of polyethylene glycol maleimide and the polypeptide of SEQ ID NO:5 operably fused to one or more peptide motifs selected from a group consisting of SEQ ID NO: 6, SEQ ID NO: 8, SEQ ID NO: 12 and SEQ ID NO: 14, wherein the CLP-PEG is crosslinked into a network using 4-(4,6-Dimethoxy-1,3,5-triazin-2-yl)-4-methylmorpholinium chloride (DMTMM) as the crosslinker and further comprising fibrinogen and a second network of 2-methacryloyloxyethyl phosphorylcholine (MPC).

2. The hydrogel as claimed in claim 1, further comprising corneal stem cells.

3. A corneal implant comprising the hydrogel as claimed in claim 1.

4. A CLP-PEG filler glue comprising the hydrogel as claimed in claim 1, wherein the concentration of DMTMM is 4% (w/v).

5. A CLP-PEG filler glue comprising the hydrogel as claimed in claim 1, wherein the concentration of CLP-PEG is 10% (w/w), the concentration of DMTMM is 2% (w/w) and the concentration of fibrinogen is 1% (w/w).

6. A method of treating a condition of the eye characterized by a corneal defect, said method comprising: a. making a limbal incision in the area affected by the corneal defect in a subject; b. inserting a collagen based ab interno patch; and c. administering the filler glue as claimed in claim 4 over the corneal defect.

7. A method of treating a condition of the eye characterized by a corneal defect, said method comprising: a. administering thrombin in the area affected by the corneal defect in a subject; and b. administering the filler glue as claimed in claim 5 over the corneal defect.

8. The hydrogel of claim 1 molded into the shape of a corneal implant.

9. The hydrogel of claim 1, wherein the concentration of DMTMM is 2% to 4% (w/v).

10. The hydrogel of claim 1, wherein the concentration of CLP-PEG is 10% to 15% (w/w), the concentration of DMTMM is 2% to 4% (w/v), and the concentration of fibrinogen is 1% (w/w).

11. The hydrogel of claim 1 molded into the shape of a corneal implant, wherein the concentration of DMTMM is 2% to 4% (w/v).

12. The hydrogel of claim 1 molded into the shape of a corneal implant, wherein the concentration of CLP-PEG is 10% to 15% (w/w), the concentration of DMTMM is 2% to 4% (w/v) and the concentration of fibrinogen is 1% (w/w).

13. The hydrogel of claim 1, wherein polyethylene glycol-maleimide has 4 to 8 arms, a molecular weight of 10 to 40 kDa, and a hexaglycerol or pentaerythritol core.

14. The hydrogel of claim 1, wherein polyethylene glycol-maleimide has 8 arms, a molecular weight of 40 kDa, and a hexaglycerol core.

15. A hydrogel comprising CLP-PEG, wherein the collagen-like peptide (CLP-PEG) comprises a conjugate of polyethylene glycol maleimide and the polypeptide of SEQ ID NO:5 or SEQ ID NO:10 operably fused to the peptide motif of SEQ ID NO: 14, wherein the CLP-PEG is crosslinked into a network using 4-(4,6-Dimethoxy-1,3,5-triazin-2-yl)-4-methylmorpholinium chloride (DMTMM) as the crosslinker.

16. The hydrogel of claim 15, further comprising components selected from the group consisting of fibrinogen, and a second network of 2-methacryloyloxyethyl phosphorylcholine (MPC).

* * * * *